US010328222B2

(12) United States Patent
Foote

(10) Patent No.: US 10,328,222 B2
(45) Date of Patent: Jun. 25, 2019

(54) VENT DEVICE FOR USE WITH A RESPIRATORY DEVICE

(71) Applicant: ResMed Limited, Bella Vista (AU)

(72) Inventor: Roger Mervyn Lloyd Foote, Eastwood (AU)

(73) Assignee: ResMed Pty Ltd (AU)

( * ) Notice: Subject to any disclaimer, the term of this patent is extended or adjusted under 35 U.S.C. 154(b) by 108 days.

(21) Appl. No.: 14/199,582

(22) Filed: Mar. 6, 2014

(65) Prior Publication Data
US 2014/0261427 A1   Sep. 18, 2014

(30) Foreign Application Priority Data

Mar. 14, 2013 (AU) ................................ 2013900885

(51) Int. Cl.
*A61M 16/00* (2006.01)
*A61M 16/06* (2006.01)
(Continued)

(52) U.S. Cl.
CPC ........ *A61M 16/0069* (2014.02); *A61M 16/06* (2013.01); *A61M 16/0875* (2013.01);
(Continued)

(58) Field of Classification Search
CPC ............ A61M 2230/005; A61M 16/06; A61M 16/20; A61M 2205/42; A61M 16/201;
(Continued)

(56) References Cited

U.S. PATENT DOCUMENTS 1,407,216 A   2/1922   Potter
3,101,736 A   8/1963   Egger
(Continued)

FOREIGN PATENT DOCUMENTS

EP   1327458 A1   7/2003
EP   2705869 A2   3/2014
(Continued)

OTHER PUBLICATIONS

International Search Report and Written Opinion for Application No. PCT/US2012/055148 dated Feb. 15, 2013.
(Continued)

*Primary Examiner* — Gregory A Anderson
*Assistant Examiner* — Victoria Murphy
(74) *Attorney, Agent, or Firm* — Botos Churchill IP Law LLP

(57) ABSTRACT

A vent device for a respiratory device, comprising one or a plurality of vents configured with a variable aperture size for communicating a flow of breathable gas. Said vent device being configured so that the cross section profile exposed to the flow of breathable gas communicating through the vent does not change as the aperture size changes. A vent device may comprise of a plurality of the said vents, wherein the aperture size of each vent may be controlled independently or together, and may be controlled according to one or more input signals from one or more sensors. Examples of suitable input signals include flow, pressure, noise, accelerometer outputs, orientation of a patient or presence of any obstructions. A patient interface or a patient conduit may comprise the vent device, or the vent device may be configured to connect with a patient interface or a patient conduit.

27 Claims, 25 Drawing Sheets

(51) Int. Cl.
*A61M 16/08* (2006.01)
*A61M 16/20* (2006.01)
*A61M 16/16* (2006.01)

(52) U.S. Cl.
CPC ....... *A61M 16/203* (2014.02); *A61M 16/0066* (2013.01); *A61M 16/0633* (2014.02); *A61M 16/0683* (2013.01); *A61M 16/0816* (2013.01); *A61M 16/0825* (2014.02); *A61M 16/0858* (2014.02); *A61M 16/16* (2013.01); *A61M 16/208* (2013.01); *A61M 2016/0027* (2013.01); *A61M 2016/0033* (2013.01); *A61M 2202/0225* (2013.01); *A61M 2205/332* (2013.01); *A61M 2205/3334* (2013.01); *A61M 2205/3368* (2013.01); *A61M 2205/3375* (2013.01); *A61M 2205/42* (2013.01); *A61M 2230/205* (2013.01); *A61M 2230/62* (2013.01); *A61M 2230/63* (2013.01)

(58) Field of Classification Search
CPC ...... A61M 2016/0018; A61M 16/0069; A61M 16/0875; A61M 2016/0027; A61M 16/0003; A62B 18/02; A62B 9/02; A61B 5/08
See application file for complete search history.

(56) References Cited

U.S. PATENT DOCUMENTS

| | | | |
|---|---|---|---|
| 4,094,492 A * | 6/1978 | Beeman | F16K 3/03 138/45 |
| 4,306,567 A * | 12/1981 | Krasner | A61B 5/0816 600/484 |
| 4,782,832 A | 11/1988 | Trimble et al. | |
| 4,796,619 A | 1/1989 | Walther | |
| 4,842,245 A | 6/1989 | Kelsey | |
| 5,370,154 A | 12/1994 | Greer | |
| 5,568,910 A | 10/1996 | Koehler et al. | |
| 6,426,716 B1 | 7/2002 | McEwan | |
| 6,446,629 B1 | 9/2002 | Takaki et al. | |
| 6,581,594 B1 * | 6/2003 | Drew | A61M 16/06 128/204.18 |
| 6,581,596 B1 | 6/2003 | Truitt et al. | |
| 6,659,101 B2 | 12/2003 | Berthon-Jones | |
| 6,722,359 B2 | 4/2004 | Chalvignac | |
| 6,745,770 B2 | 6/2004 | McAuliffe et al. | |
| 7,059,325 B2 | 6/2006 | Hollis | |
| 8,528,562 B2 | 9/2013 | Smith et al. | |
| 2001/0009153 A1 * | 7/2001 | Pessala | A61M 16/0051 128/204.23 |
| 2003/0075176 A1 | 4/2003 | Fukunaga et al. | |
| 2004/0007232 A1 | 1/2004 | Rochat | |
| 2004/0144383 A1 | 7/2004 | Thomas et al. | |
| 2005/0126648 A1 | 6/2005 | Vu et al. | |
| 2006/0060200 A1 | 3/2006 | Ho et al. | |
| 2006/0090762 A1 | 5/2006 | Hegde et al. | |
| 2007/0033793 A1 | 2/2007 | Schlosser et al. | |
| 2008/0047560 A1 | 2/2008 | Veliss et al. | |
| 2008/0283060 A1 | 11/2008 | Bassin | |
| 2008/0302364 A1 | 12/2008 | Garde et al. | |
| 2009/0044808 A1 | 2/2009 | Guney et al. | |
| 2009/0050156 A1 | 2/2009 | Ng et al. | |
| 2009/0203972 A1 | 8/2009 | Heneghan et al. | |
| 2009/0260631 A1 | 10/2009 | Aubonnet et al. | |
| 2010/0000534 A1 | 1/2010 | Kooij et al. | |
| 2010/0043796 A1 | 2/2010 | Meynink et al. | |
| 2010/0051034 A1 | 3/2010 | Howard et al. | |
| 2010/0258123 A1 | 10/2010 | Somaiya et al. | |
| 2010/0307500 A1 | 12/2010 | Armitstead | |
| 2010/0326447 A1 | 12/2010 | Loomas et al. | |
| 2011/0126832 A1 | 6/2011 | Winter et al. | |
| 2012/0065533 A1 * | 3/2012 | Carrillo, Jr. | A61B 5/083 600/532 |
| 2013/0213401 A1 | 8/2013 | Haibach | |
| 2014/0283831 A1 | 9/2014 | Foote et al. | |

FOREIGN PATENT DOCUMENTS

| | | | |
|---|---|---|---|
| WO | 1998/004310 A1 | 2/1998 | |
| WO | 1998/034665 A1 | 8/1998 | |
| WO | 2000/078381 A1 | 12/2000 | |
| WO | WO 0126722 A1 * | 4/2001 | ............ A61M 16/06 |
| WO | 2002/053217 | 7/2002 | |
| WO | 2004/073778 A1 | 9/2004 | |
| WO | 2005/051468 | 6/2005 | |
| WO | 2005/063328 A1 | 7/2005 | |
| WO | 2006/074513 A1 | 7/2006 | |
| WO | 2006/102708 A1 | 10/2006 | |
| WO | 2006130903 A1 | 12/2006 | |
| WO | 2008/055308 | 5/2008 | |
| WO | 2009/052560 A1 | 4/2009 | |
| WO | 2010/135785 A1 | 12/2010 | |
| WO | 2011006199 A1 | 1/2011 | |
| WO | 2012012835 A2 | 2/2012 | |
| WO | 2013040198 A2 | 3/2013 | |

OTHER PUBLICATIONS

International Search Report for Application No. PCT/AU2014/000263 dated Jun. 11, 2014.
International Written Opinion for Application PCT/AU2014/000263 dated Jun. 11, 2014.
Partial European Search Report for Application No. 13183779.1 dated Dec. 11, 2013.

* cited by examiner

VENT DEVICE FOR USE WITH A RESPIRATORY DEVICE

CROSS-REFERENCE TO RELATED APPLICATIONS

The present application claims priority from Australian Provisional Patent Application No. AU 2013900885 filed Mar. 14, 2013, the disclosure of which is hereby incorporated herein by reference.

STATEMENT REGARDING FEDERALLY SPONSORED RESEARCH OR DEVELOPMENT

Not Applicable

THE NAMES OF PARTIES TO A JOINT RESEARCH DEVELOPMENT

Not Applicable

SEQUENCE LISTING

Not Applicable

BACKGROUND OF THE INVENTION (1) Field of the Invention

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist. Some examples of respiratory disorders include: Obstructive Sleep Apnea (OSA), Cheyne Stokes Respiration (CSR), Obesity Hyperventilation Syndrome (OHS), Chronic Obstructive Pulmonary Disease (COPD), Neuromuscular Disease (NMD) or chest wall disorders.

Otherwise healthy individuals may take advantage of systems and devices to prevent respiratory disorders from arising.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

Seal-forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2: 2007, 10 cmH$_2$O pressure at 1 m)

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10 cmH$_2$O)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

PAP Device

The air at positive pressure is typically supplied to the airway of a patient by a PAP device such as a motor-driven blower. The outlet of the blower is typically connected via a flexible delivery conduit to a patient interface as described above.

Humidifier

Respiratory apparatuses commonly have the ability to alter the humidity of the breathable gas in order to reduce drying of the patient's airway and consequent patient discomfort and associated complications. The use of a humidifier placed between the flow generator and the patient interface produces humidified gas that minimizes drying of the nasal mucosa and increases patient airway comfort. In addition, in cooler climates warm air applied generally to the face area in and about the patient interface is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator, and a gas outlet adapted to be connected to a patient conduit that delivers the humidified gas to the patient's mask.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology comprises a vent, the vent configured with a variable aperture size for communicating a flow of breathable gas. Another aspect of the present technology is configuration of the vent such that the cross section profile exposed to the flow of breathable gas traversing through the vent remains constant as the vent aperture size changes.

Another form of the present technology comprises a vent device comprising a plurality of vents. Another key aspect of this form of the present technology is that the aperture size of each vent may be controlled independently or together. Furthermore, the aperture size of each vent may be controlled according to one or more input signals from one or more sensors, suitable examples of the one or more sensors may include flow, pressure, noise, accelerometer outputs, orientation of a patient or presence of any obstructions.

Another aspect of one form of the present technology is the control of size of cross-section areas of a plurality of vents according to one or more input signals from one or more sensors. Examples of suitable input signals include flow, pressure, noise, accelerometer outputs, orientation of a patient or presence of any obstructions.

Another aspect of one form of the present technology is a vent device comprising a plurality of vents, and a plurality of microphones, each vent comprising a variable cross-section area for communication of a flow of breathable gas and the microphones configured to produce signals indicating the noise level generated by a flow of breathable gas communicating through each vent, wherein the cross-section area of each vent is controlled according to the signals produced by the microphones.

Another aspect of one form of the present technology is a vent device comprising a plurality of vents and an accelerometer, each vent comprising a variable cross-section area for communication of a flow of breathable gas and the accelerometer configured to produce a signal indicating orientation of the patient or the orientation of the vent device, wherein the cross-section area of each vent is controlled according to the signal produced by the accelerometer.

Another aspect of one form of the present technology is a vent device comprising a plurality of vents, each vent comprising a variable cross-section area for communication of a flow of breathable gas, wherein the cross-section area of each vent is controlled according to an output from a pressure sensor, wherein the pressure sensor is measuring a pressure of the flow of breathable gas delivered to the patient.

Another aspect of one form of the present technology is a vent device comprising a plurality of vents, each vent comprising a variable cross-section area for communication of a flow of breathable gas, wherein the cross-section area of each vent is controlled according to an output from a flow sensor, wherein the flow sensor is measuring a flow rate of the flow of breathable gas delivered to the patient.

Another aspect of one form of the present technology is a vent device comprising a plurality of vents, each vent comprising a variable cross-section area for communication of a flow of breathable gas, wherein the cross-section area of each vent is controlled according to an aspect of the patient's breath waveform.

A yet another aspect of the current technology is a patient interface comprising a vent device.

A yet another aspect of the current technology is a patient conduit comprising a vent device.

A yet another aspect of the current technology is a vent device configured to couple with a patient conduit or a patient interface.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

Treatment Systems

Therapy
Respiratory System

Figure 1A:
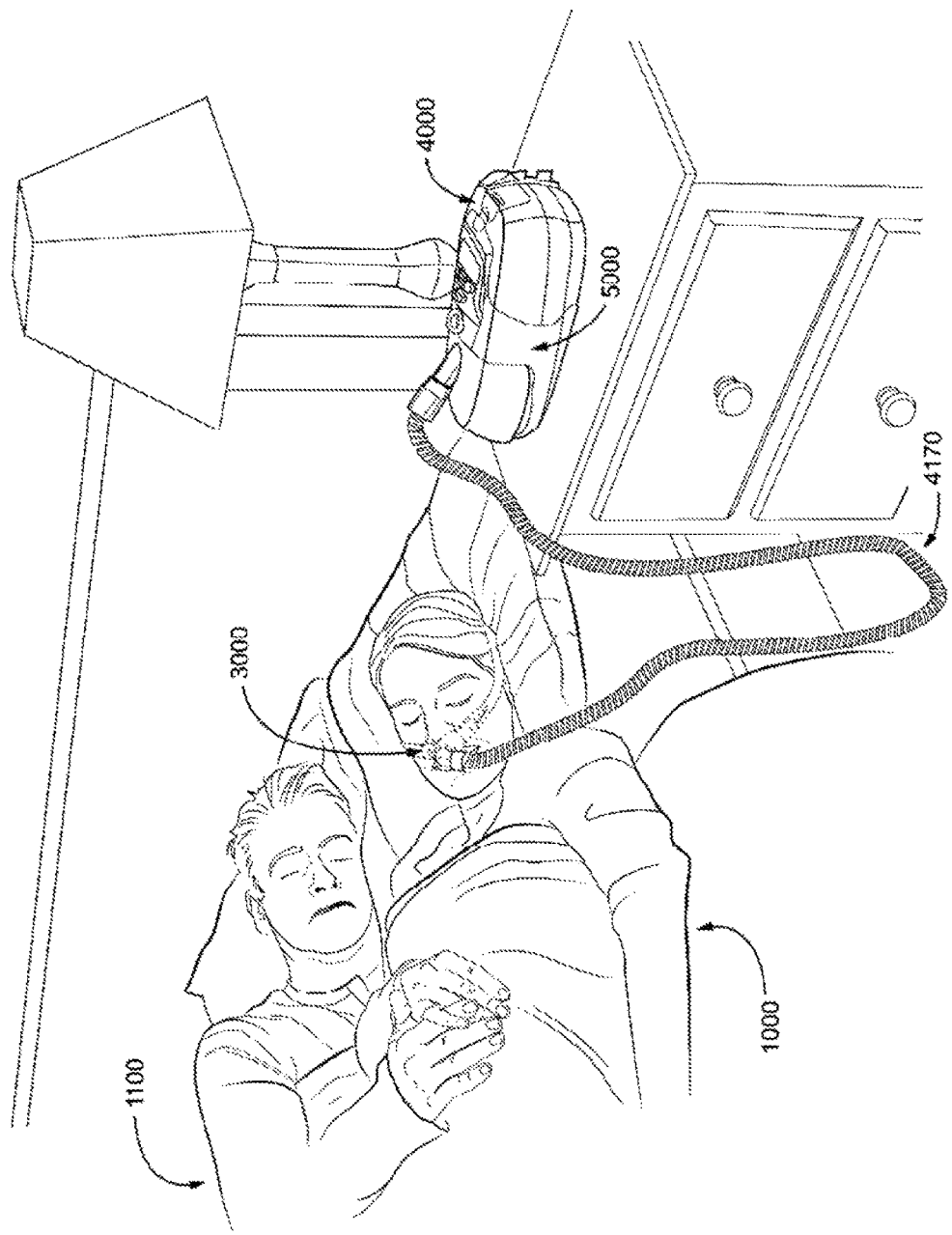
FIG. 1A shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.
Figure 1B:
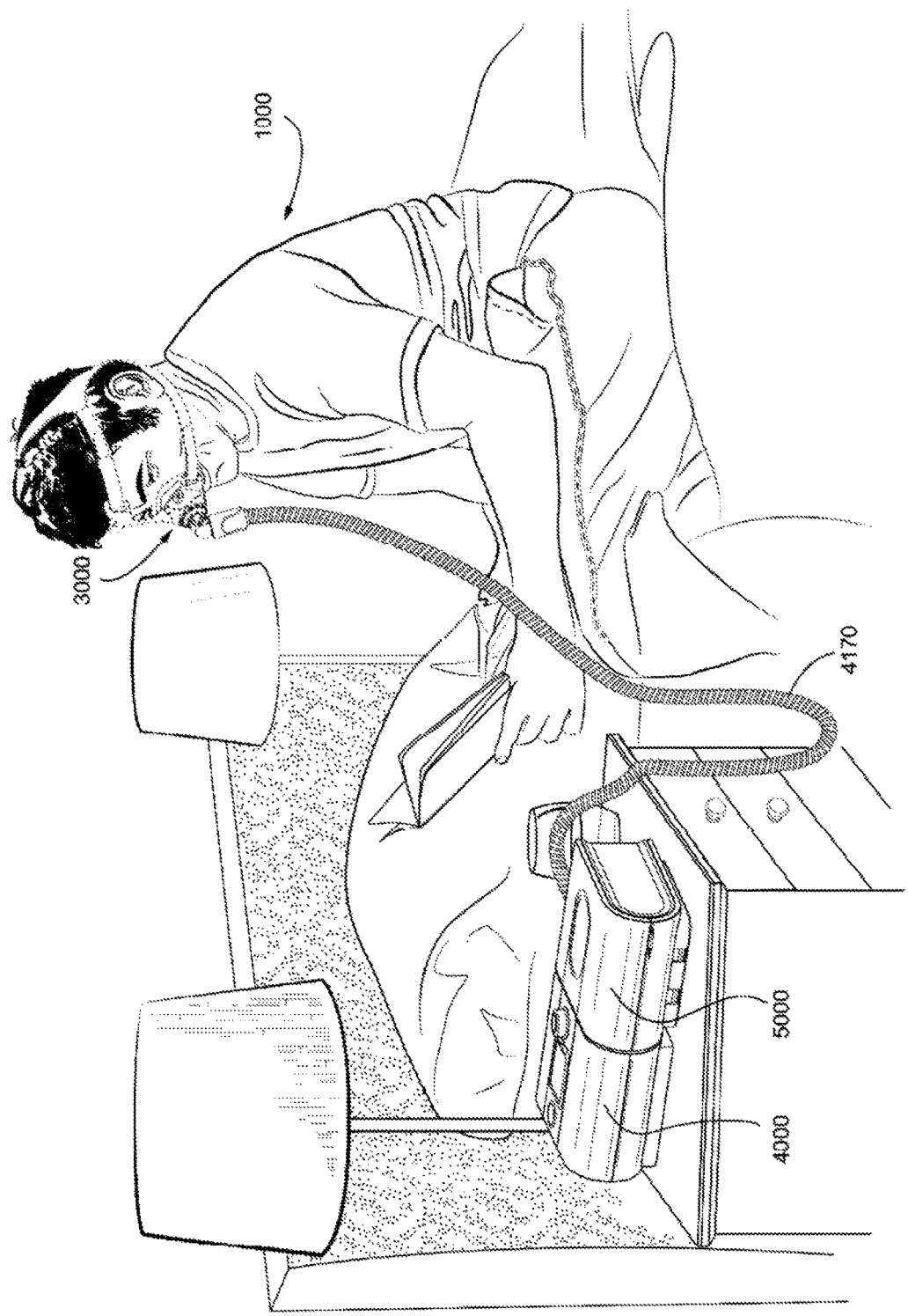
FIG. 1B shows a PAP device in use on a patient with a nasal mask.
Figure 1C:
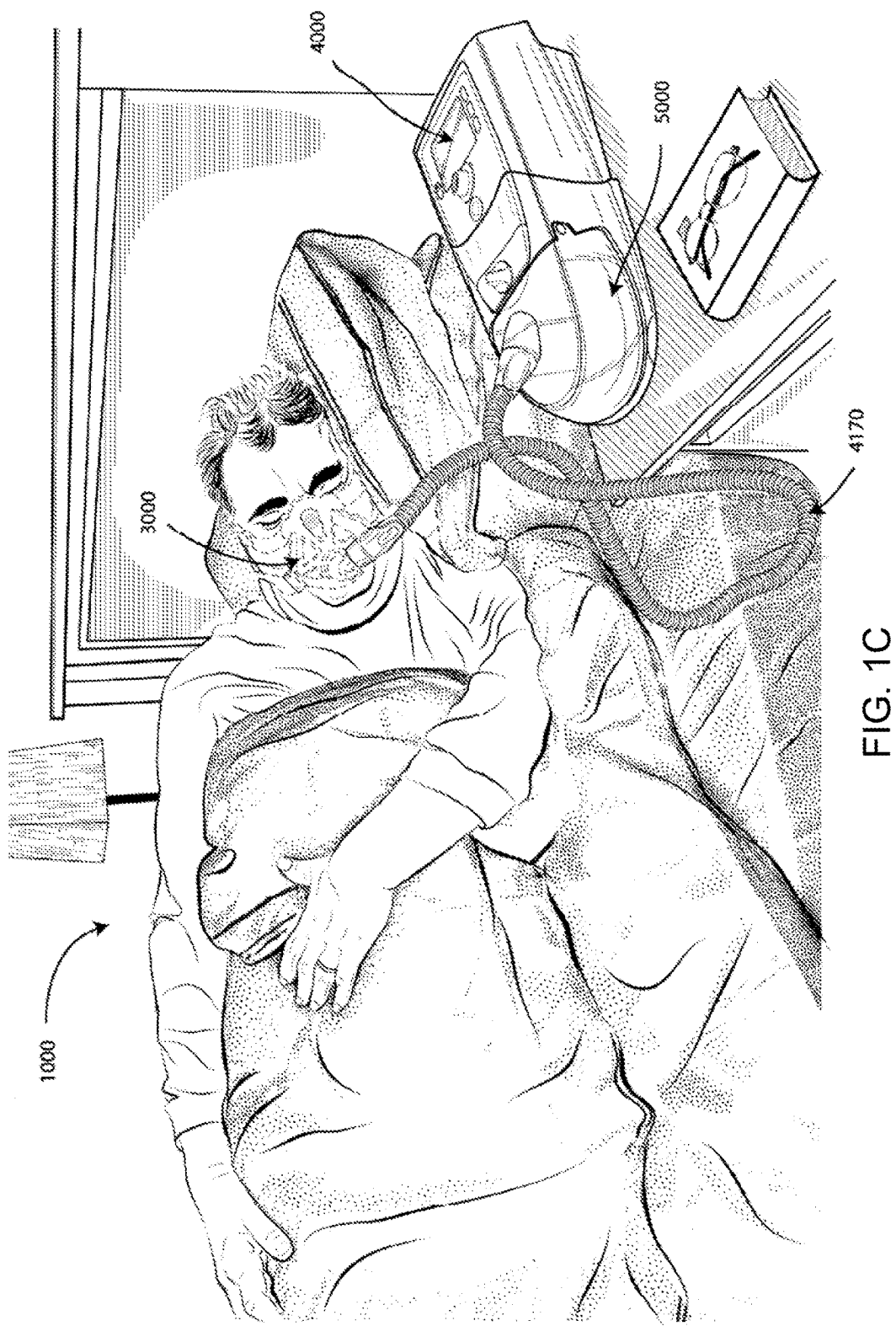
FIG. 1C shows a PAP device in use on a patient with a full-face mask.
Figure 2A:
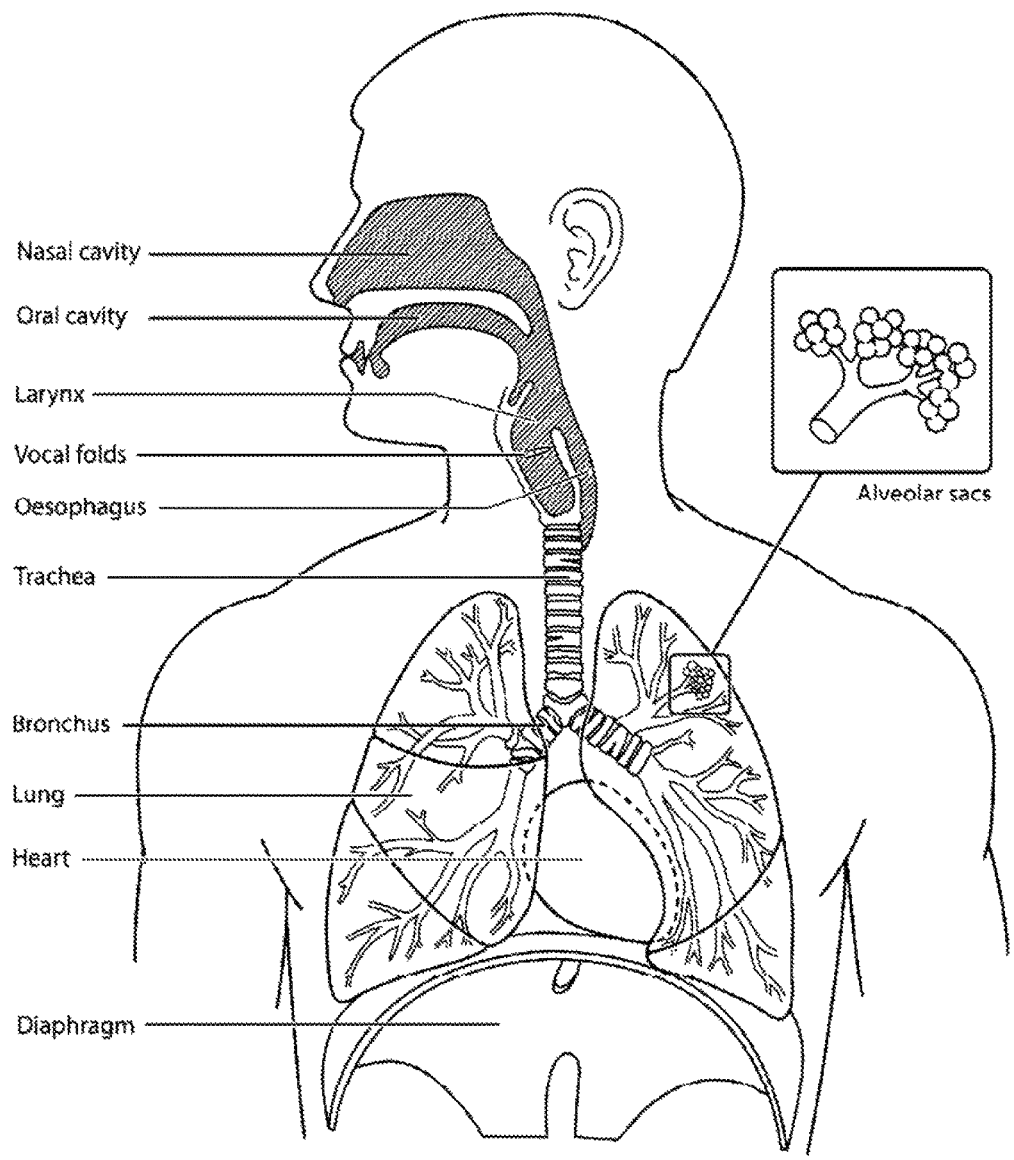

FIG. 2A shows an overview of a human respiratory system including the nasal and oral cavities, the larynx, vocal folds, oesophagus, trachea, bronchus, lung, alveolar sacs, heart and diaphragm.

Figure 2B:
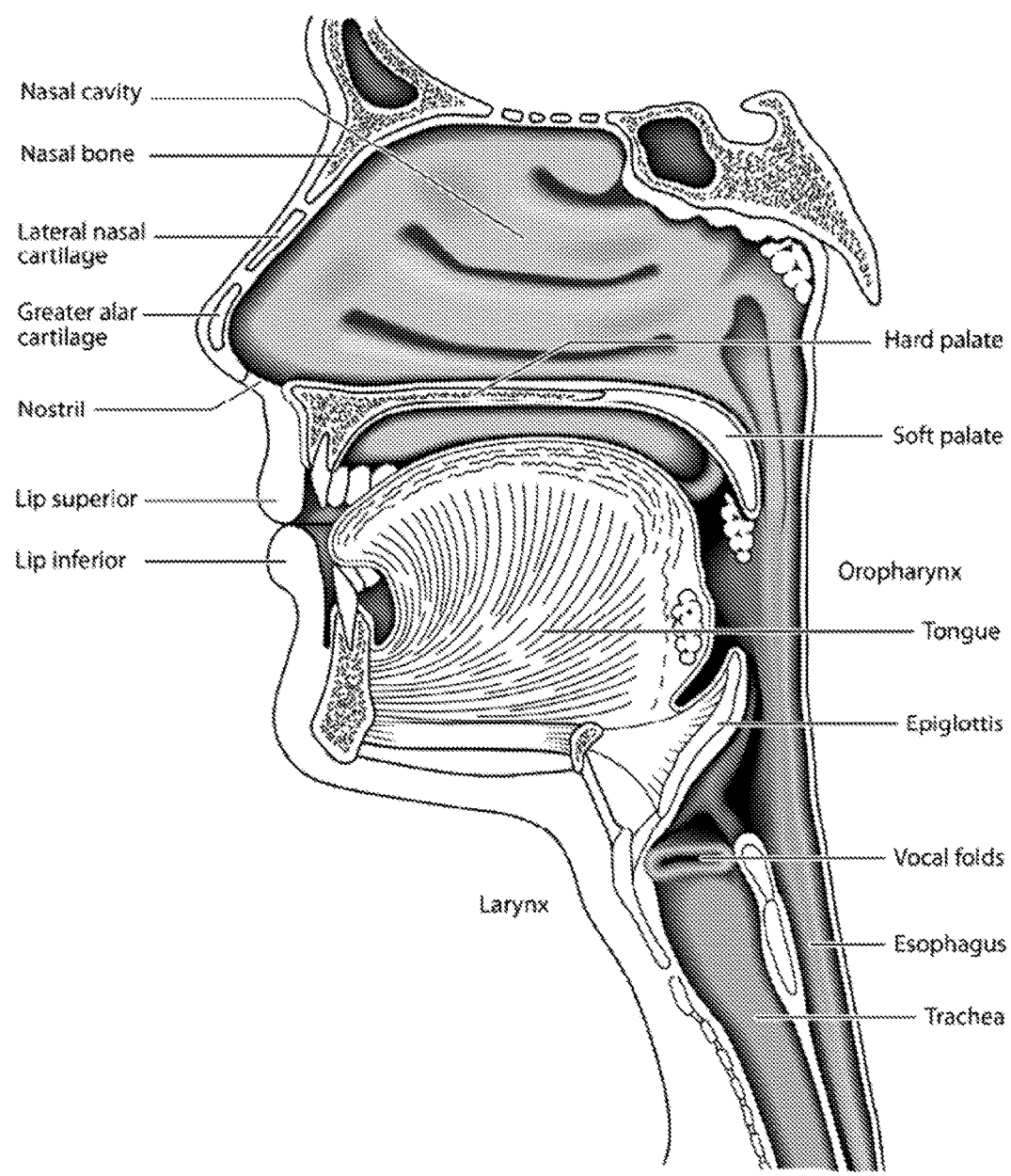

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Facial Anatomy

Figure 2C:
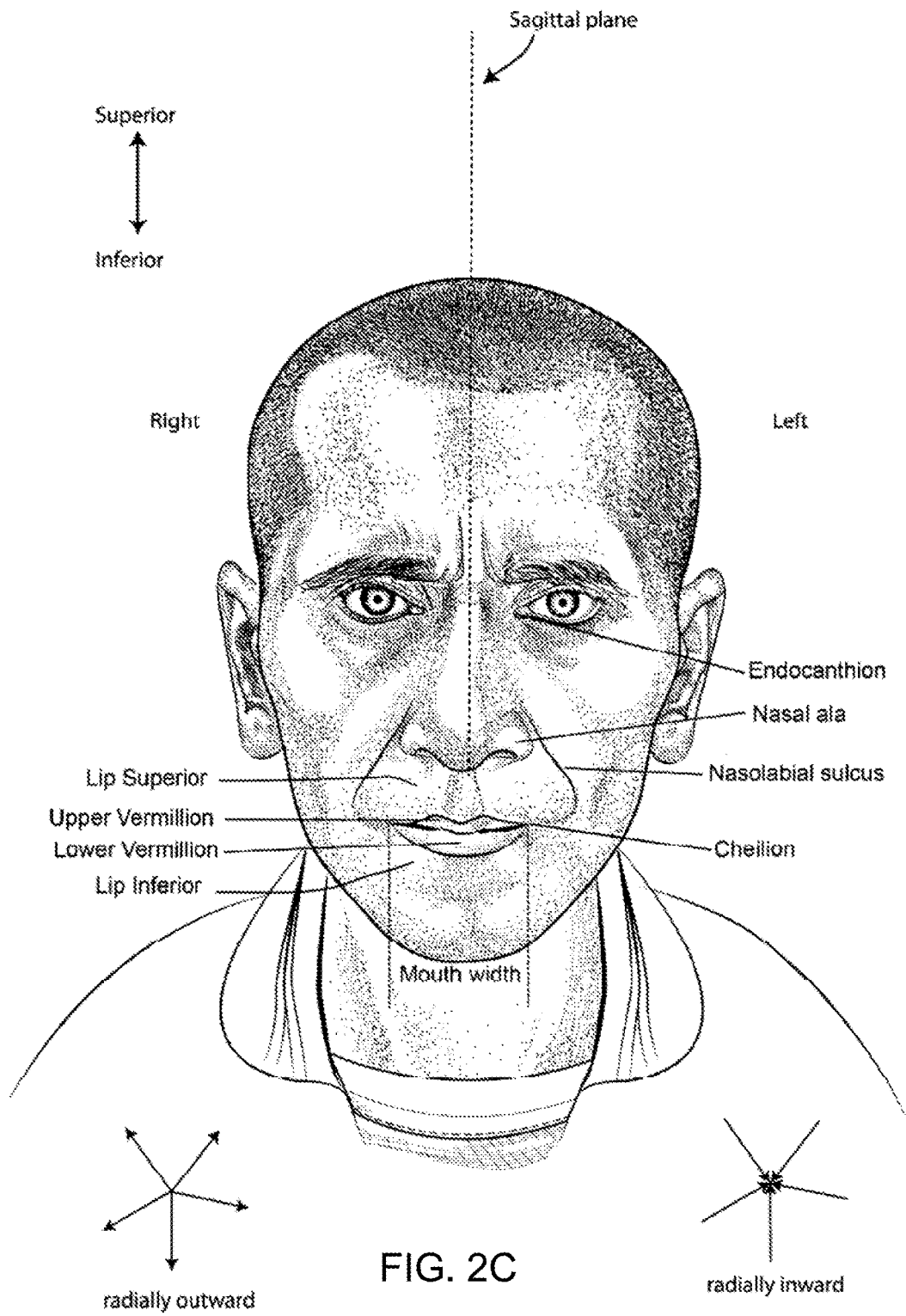

FIG. 2C is a front view of a face with several features of surface anatomy identified including the lip superior, upper vermillion, lower vermillion, lip inferior, mouth width, endocanthion, a nasal ala, nasolabial sulcus and cheilion.

Patient Interface

Figure 3A:
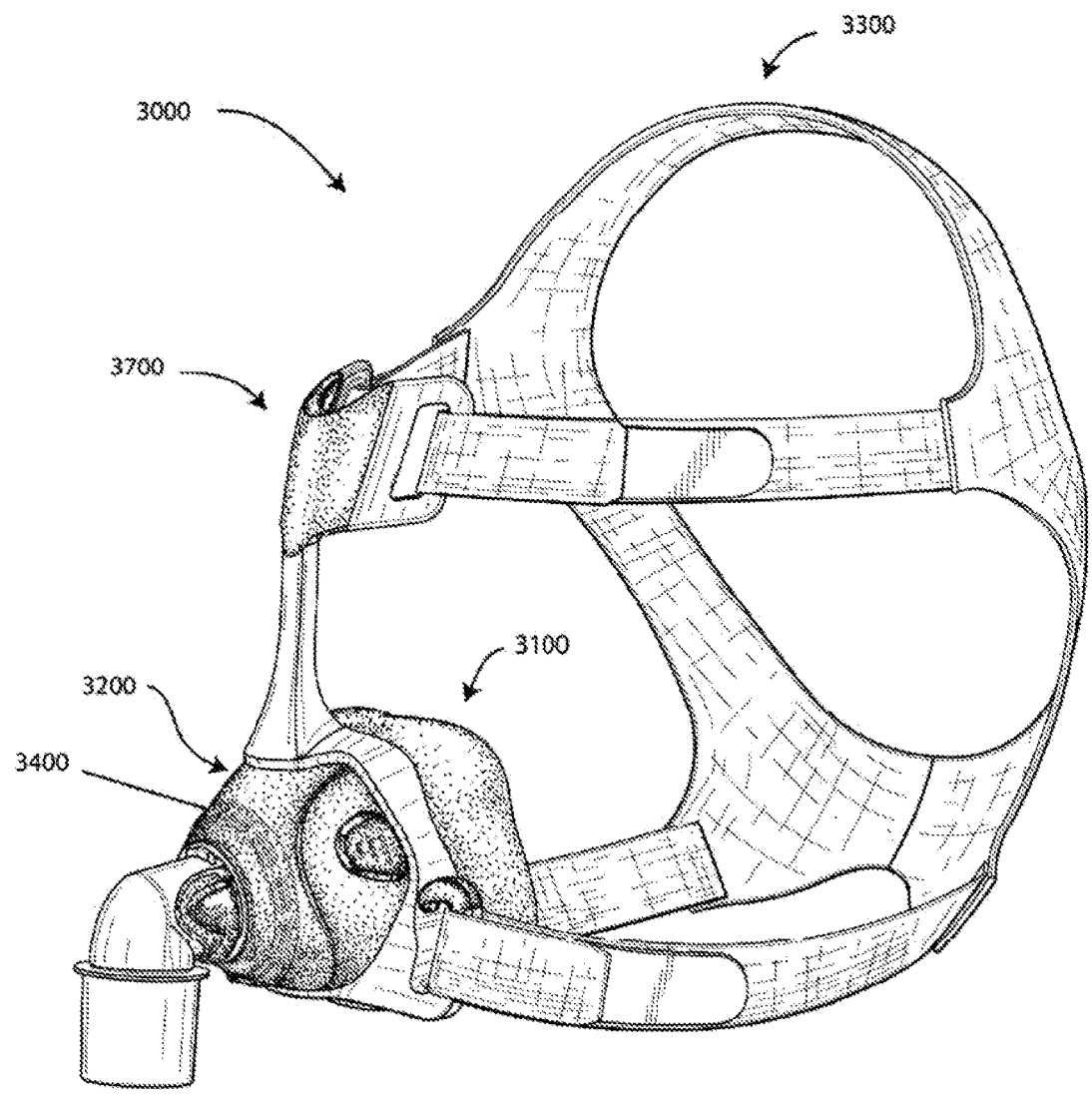

FIG. 3A shows an example of a patient interface known in the prior art.

PAP Device

Figure 4A:
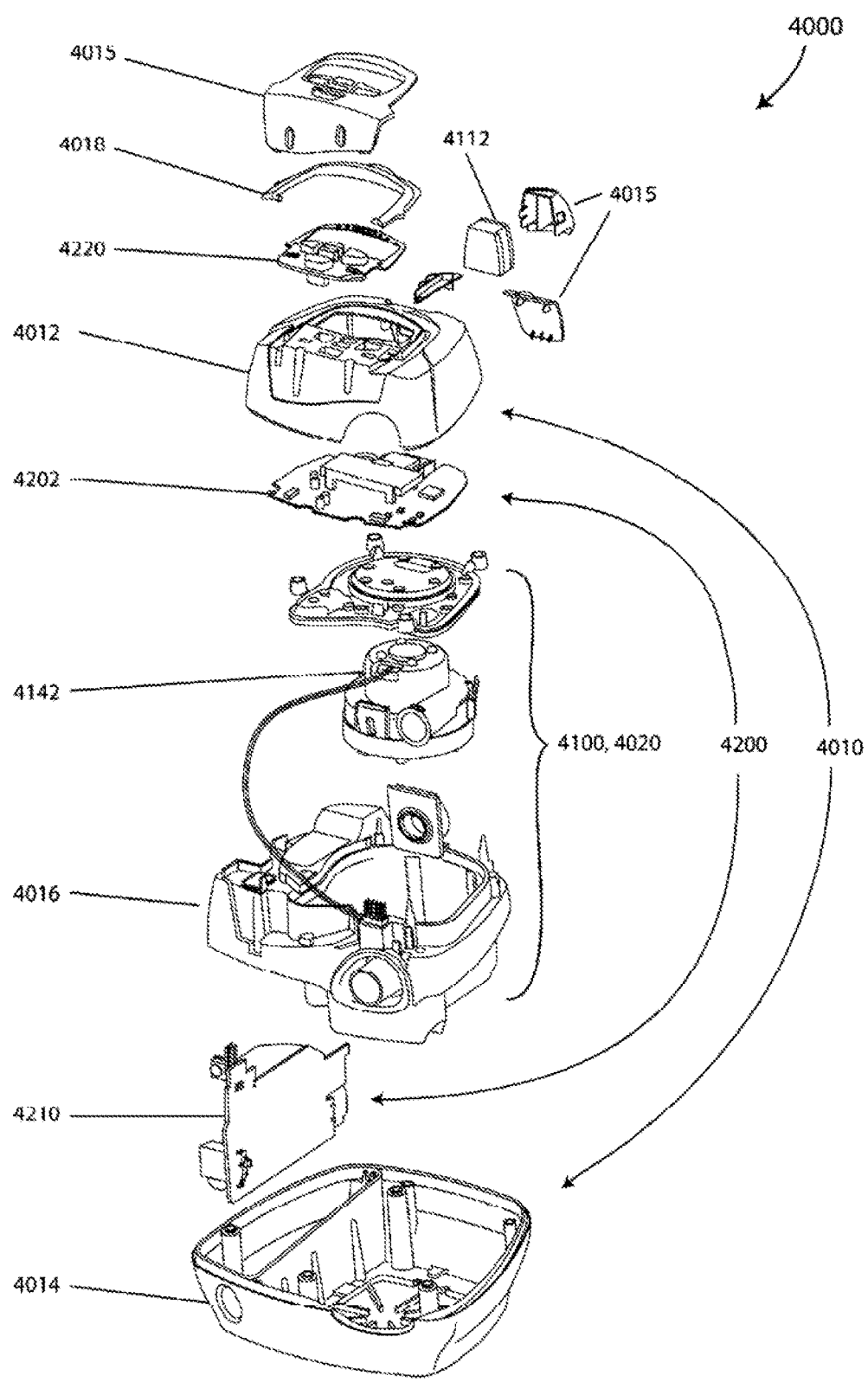

FIG. 4A shows a PAP device in accordance with one form of the present technology.

Humidifier

Figure 5A:
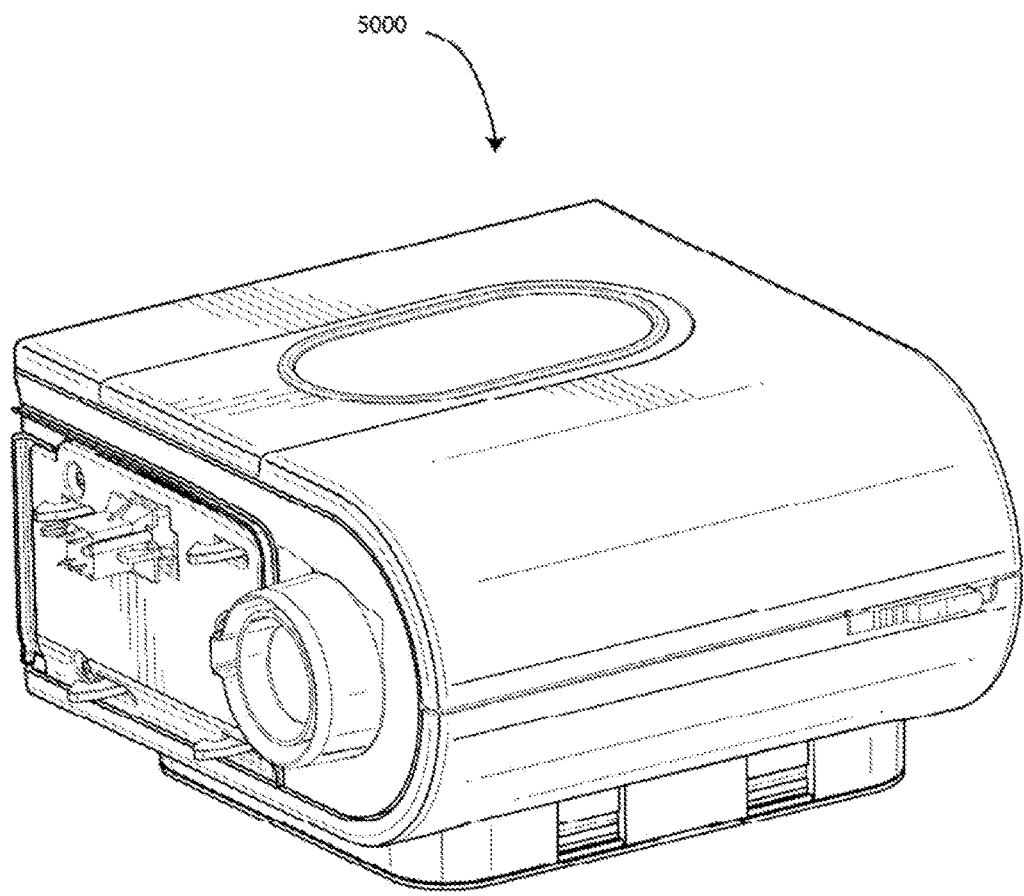

FIG. 5A shows a humidifier in accordance with one aspect of the present technology.

Breathing Waveforms

Figure 6A:
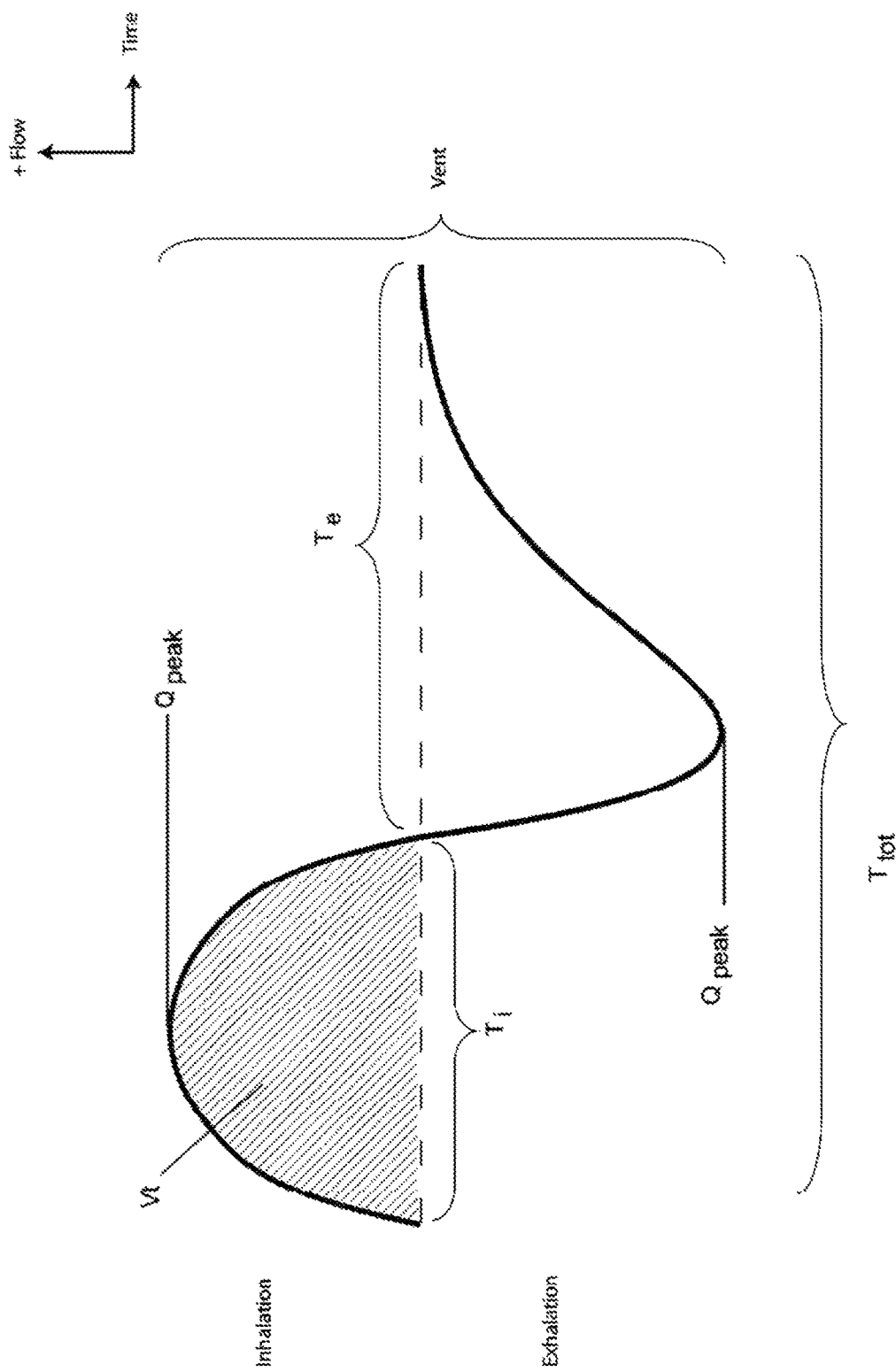

FIG. 6A shows a model typical breath waveform of a person while sleeping, the horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

Figure 7:
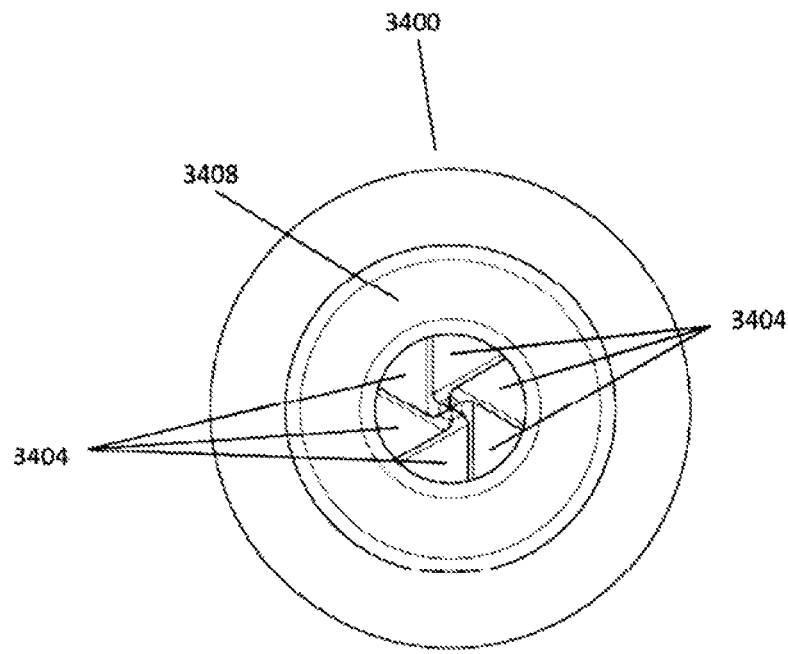
Figure 8:
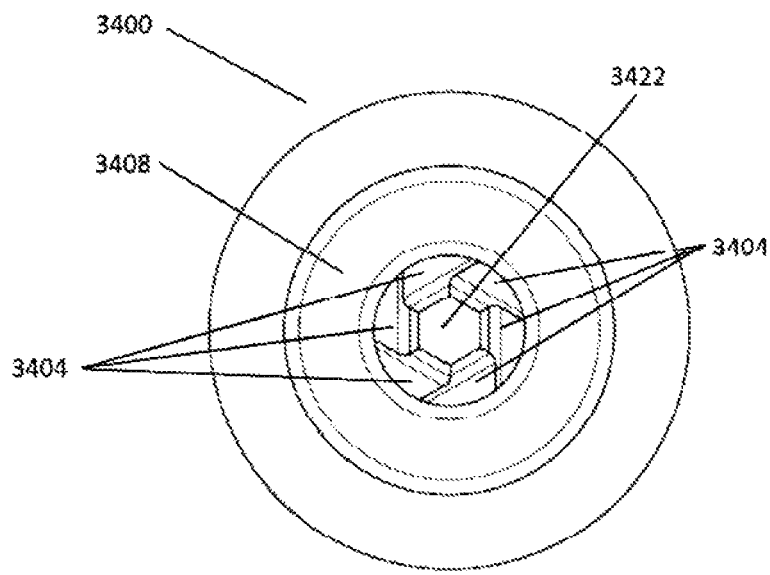
Figure 9:
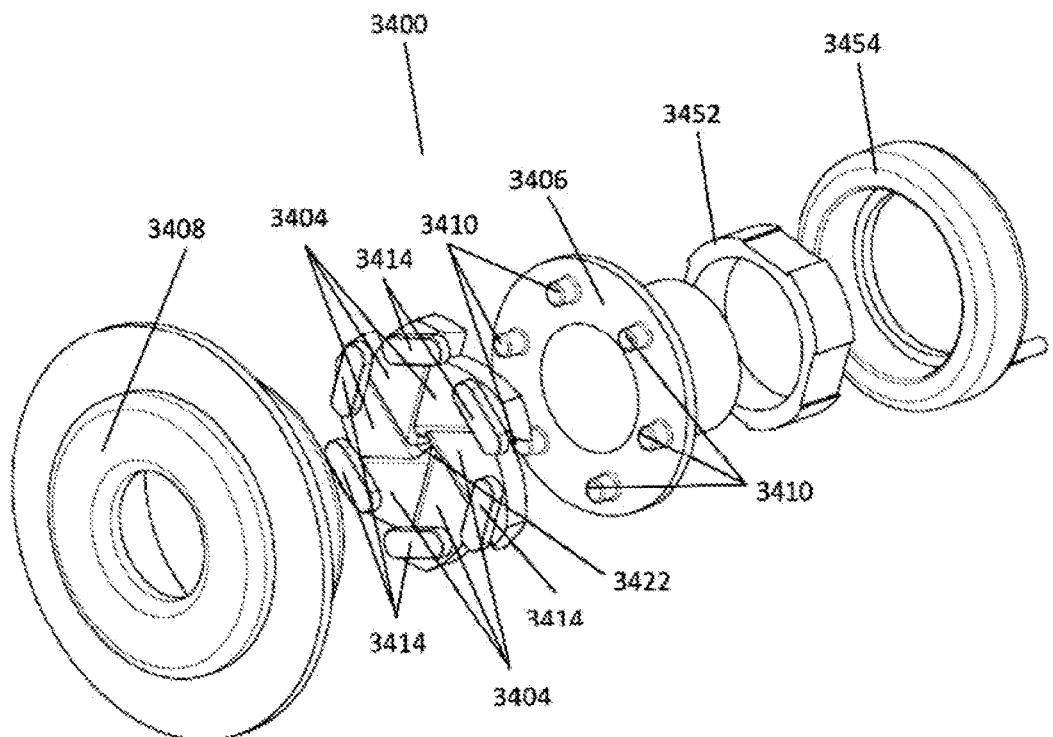
Figure 10:
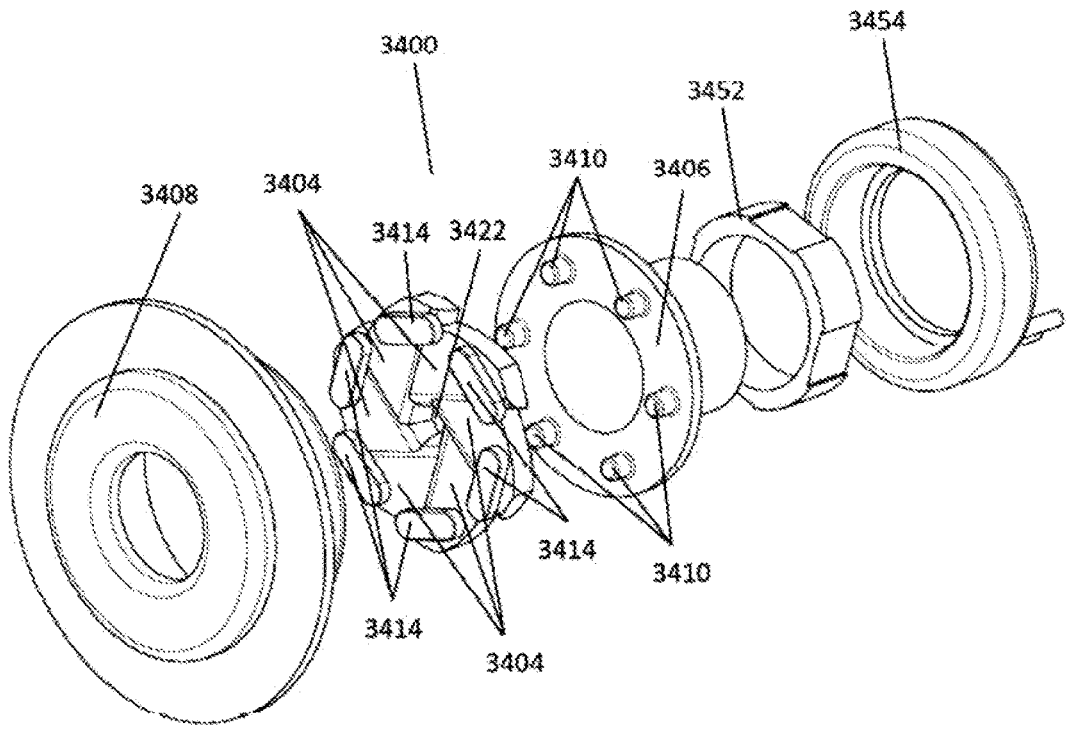
Figure 11:
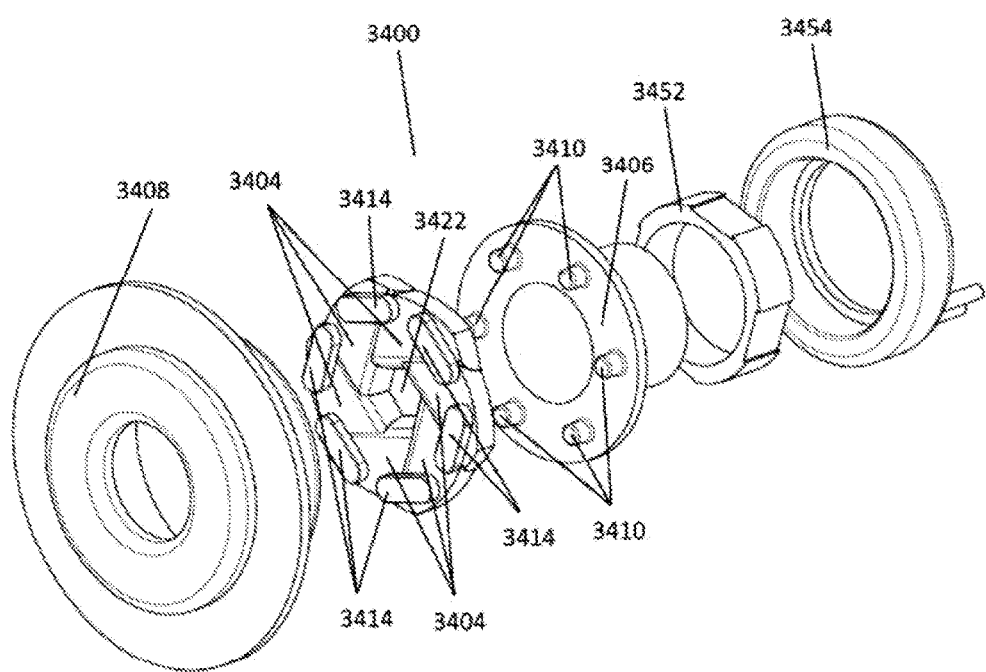
Figure 12A:
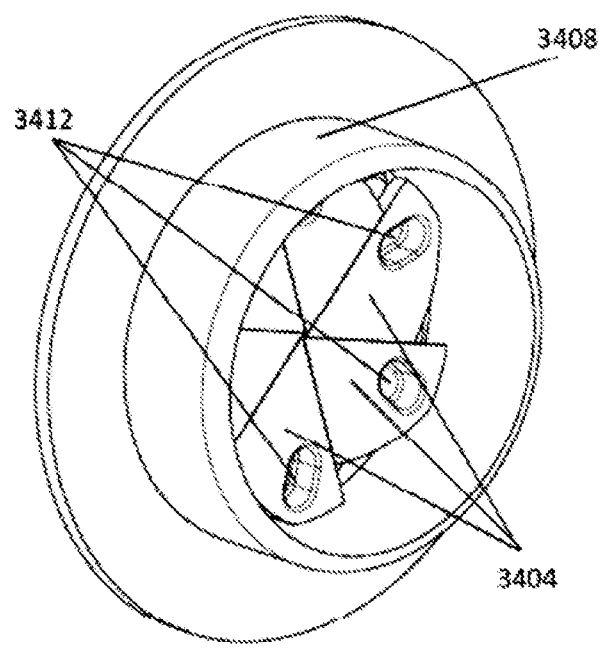
Figure 12B:
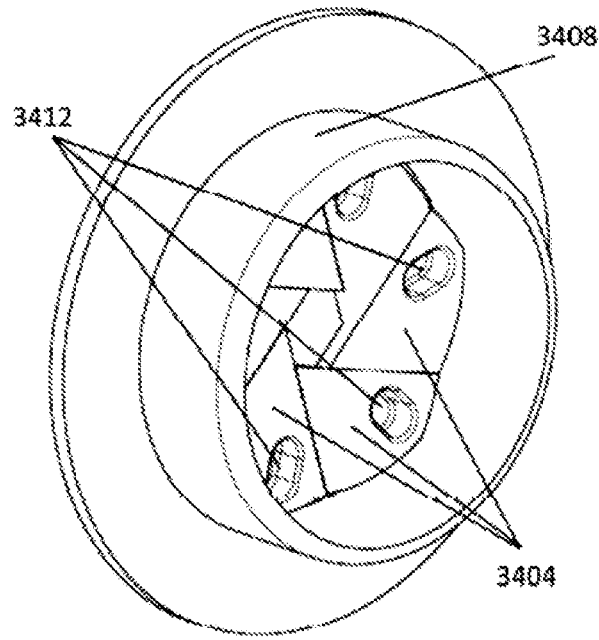
Figure 13:
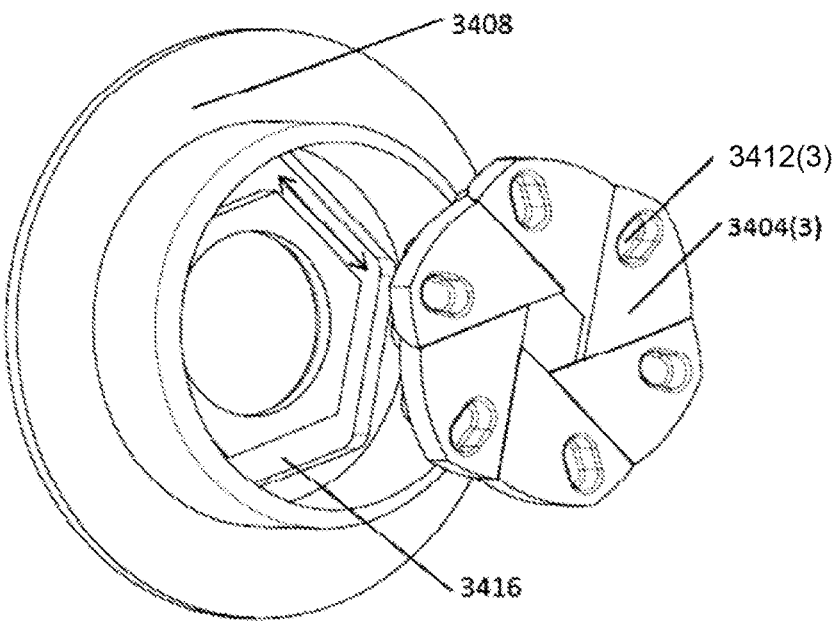
Figure 14A:
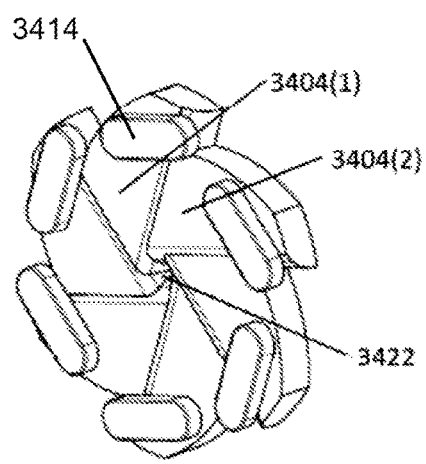
Figure 14B:
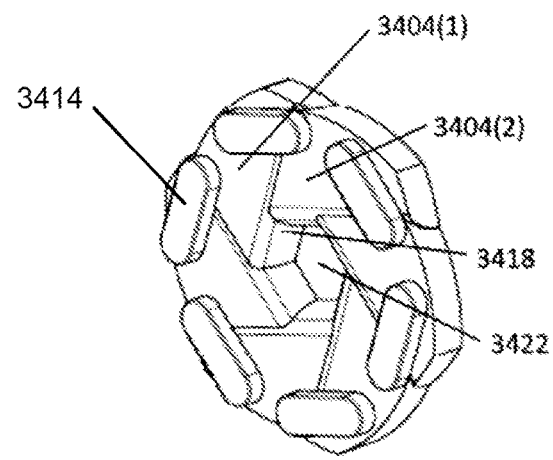
Figure 15:
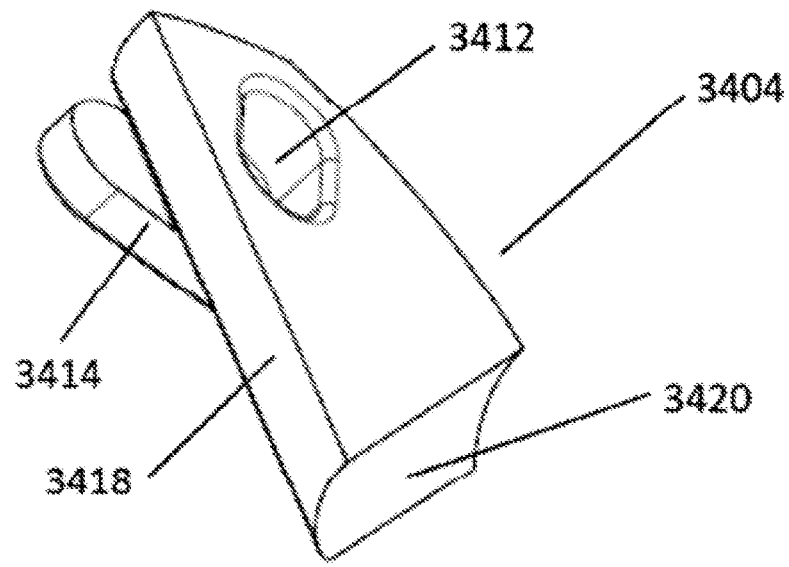
Figure 16:
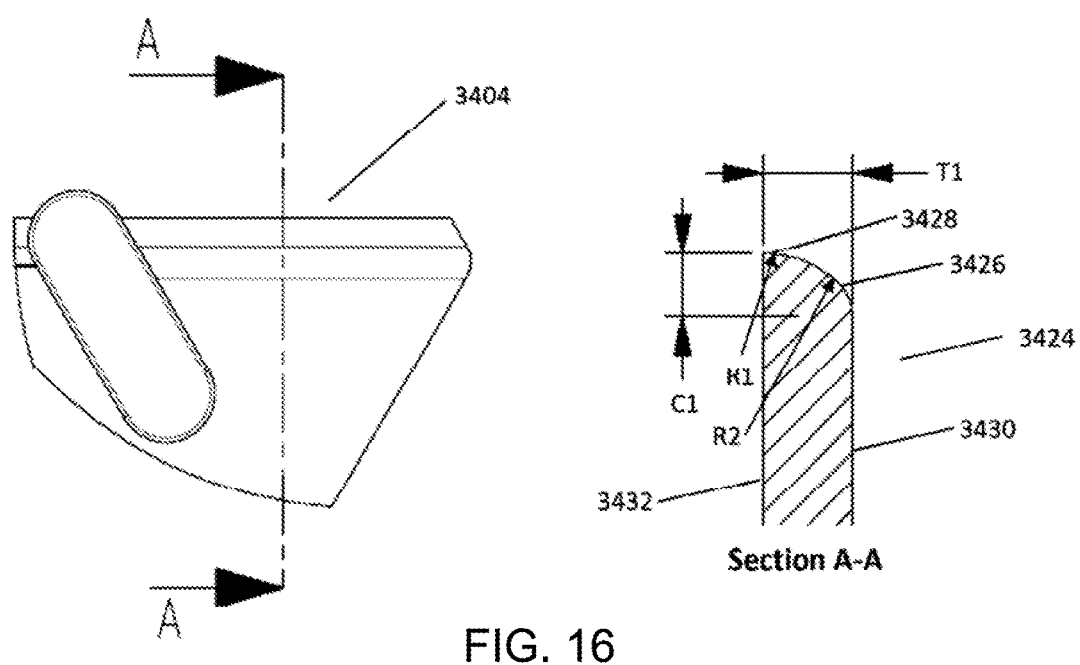
Figure 17:
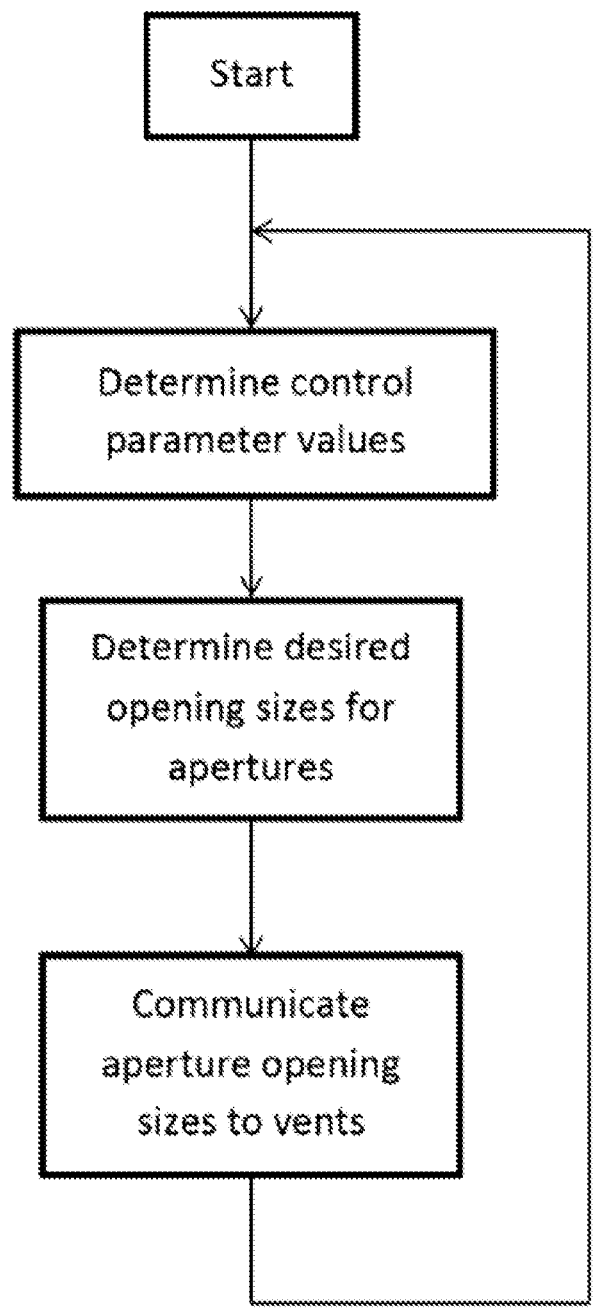
Figure 18:
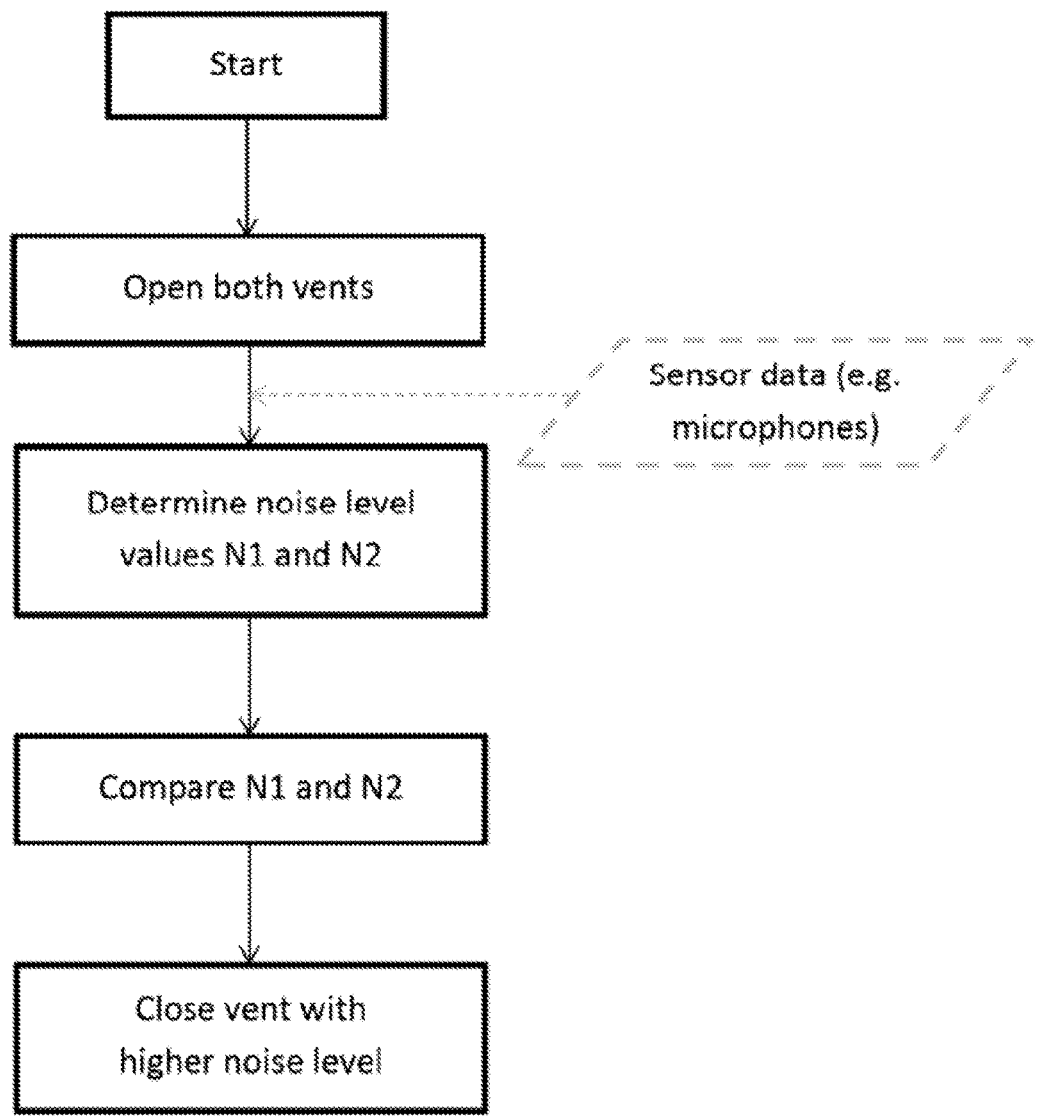
Figure 19:
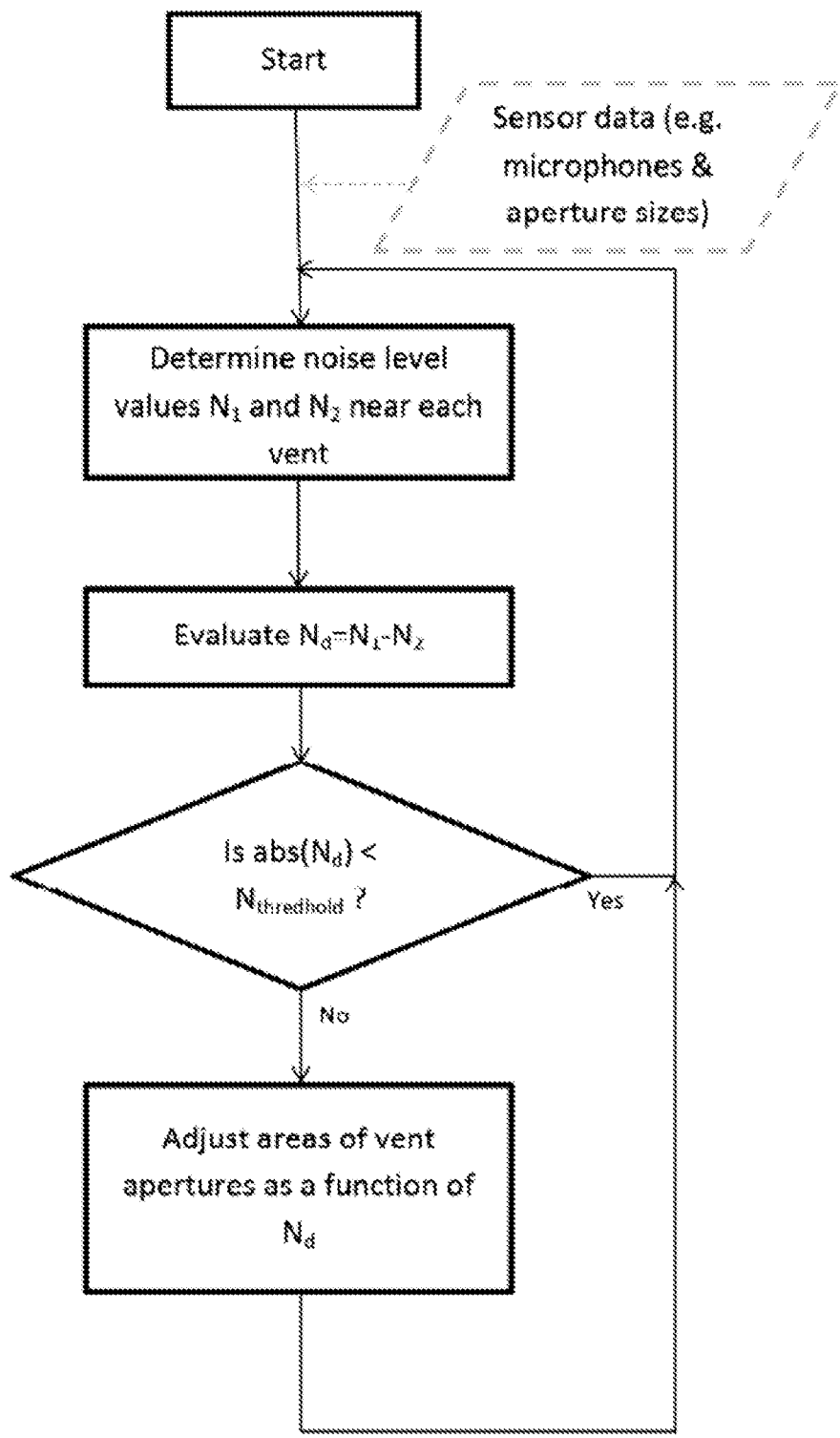
Figure 20:
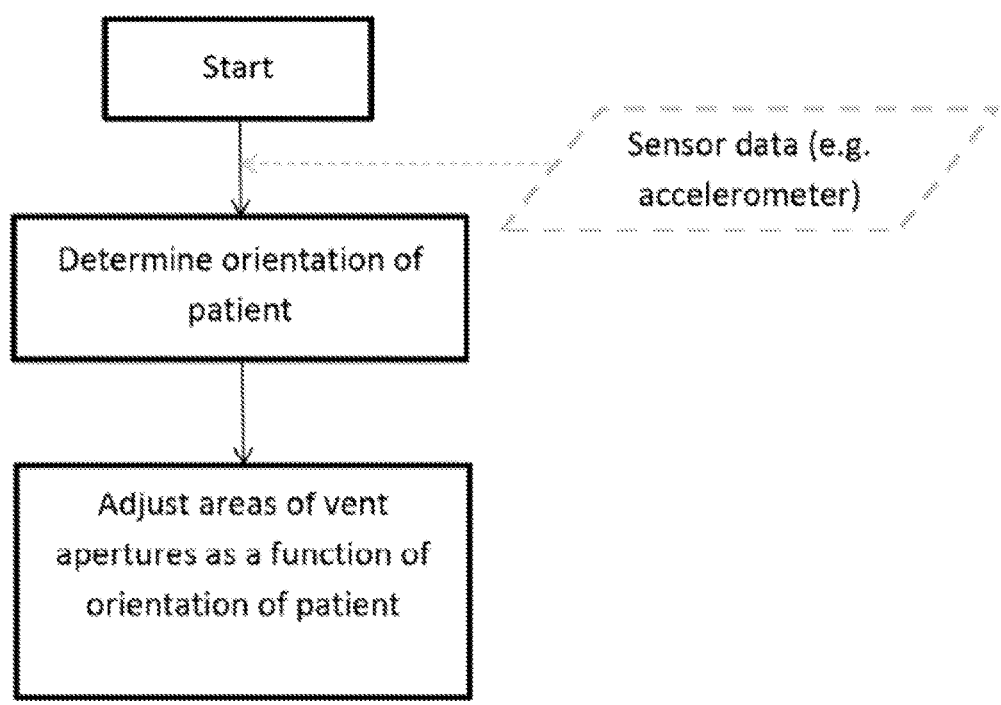
Figure 21:
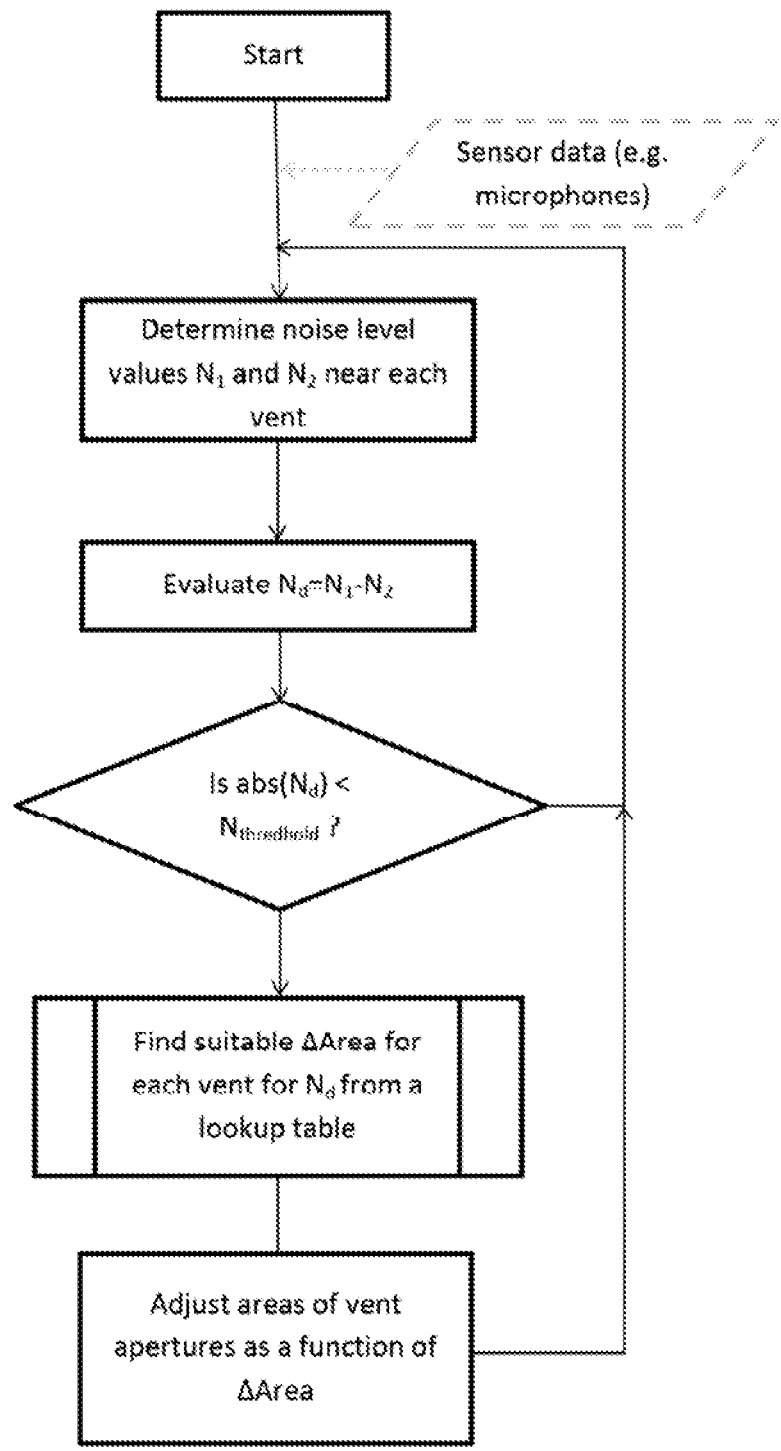
Figure 22:
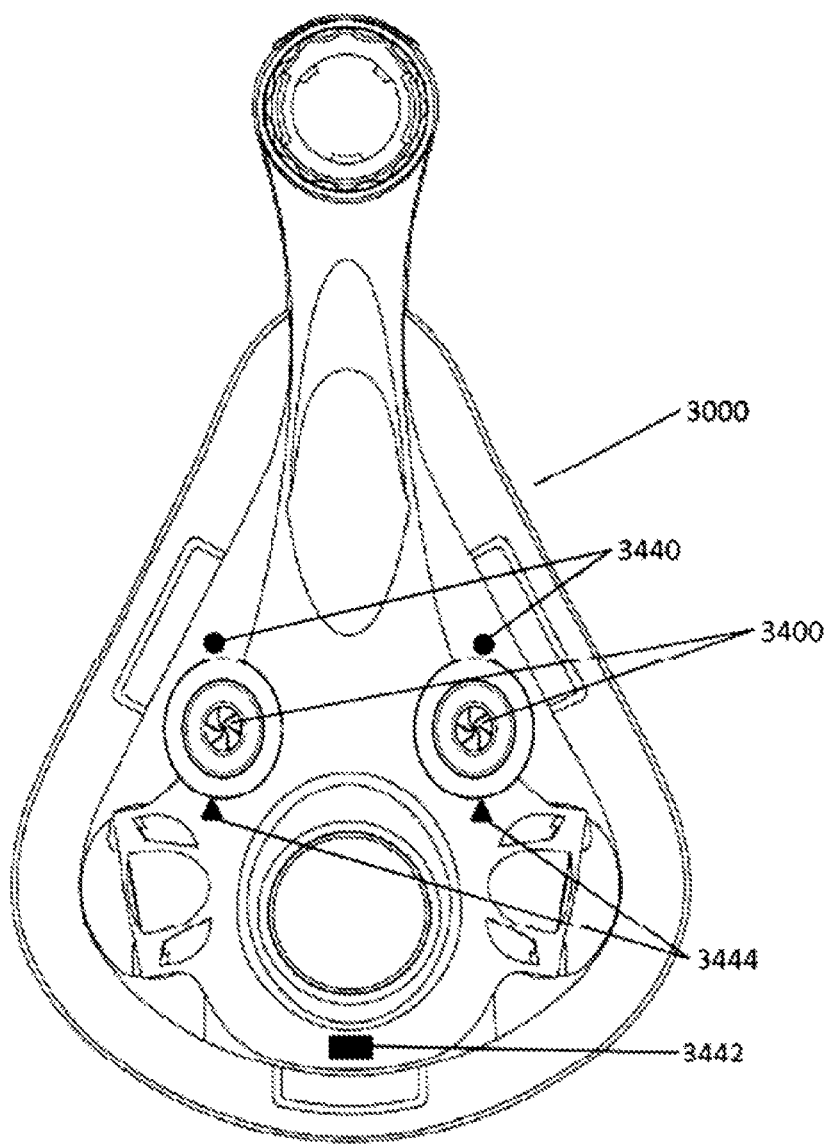
Figure 23A:
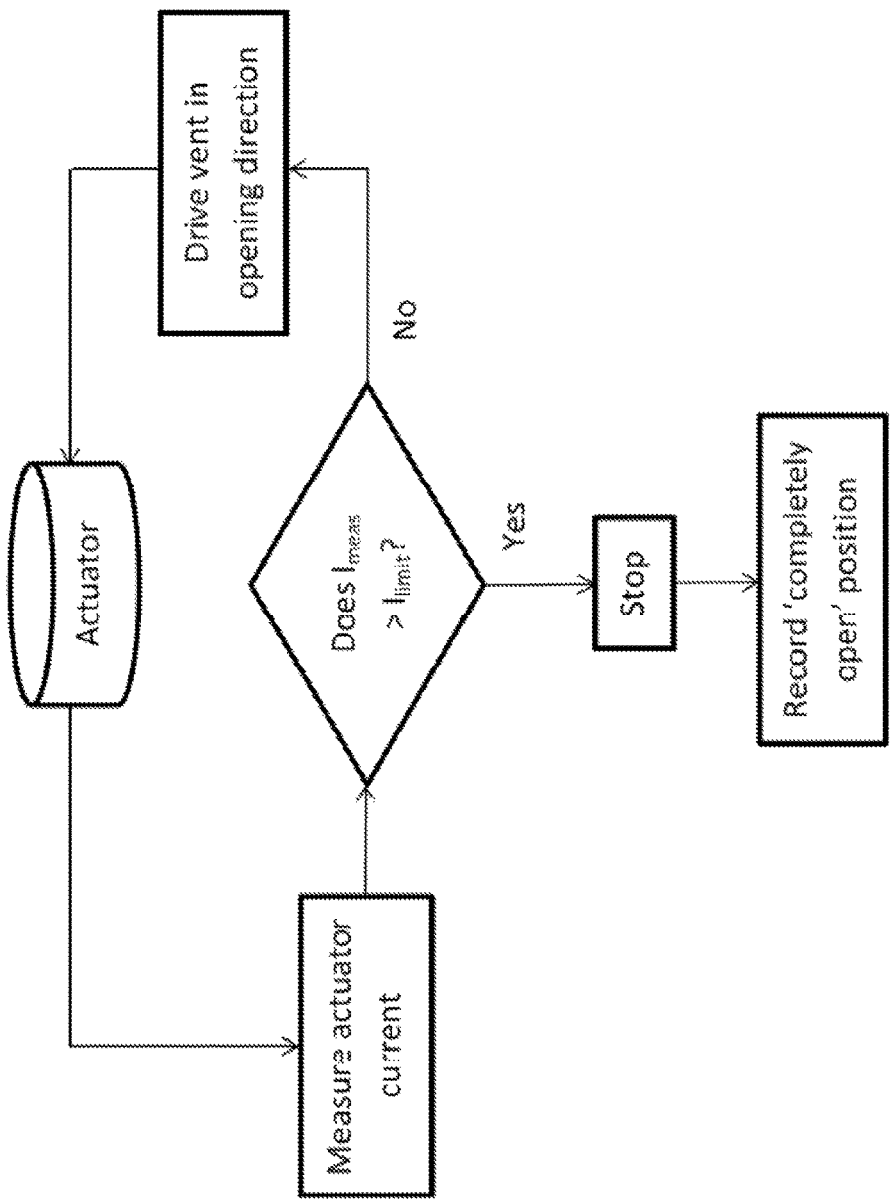
Figure 23B:
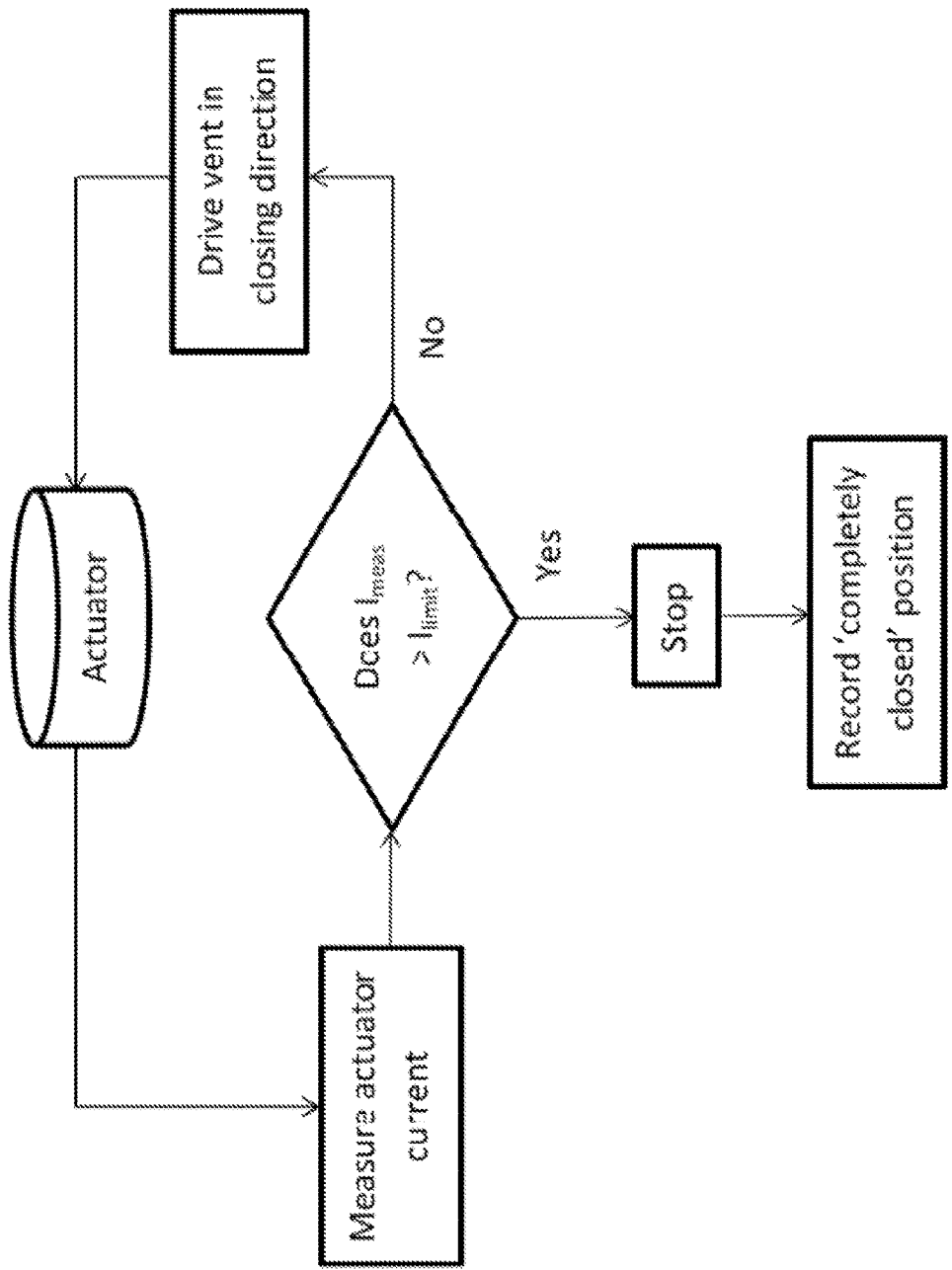
Figure 24:
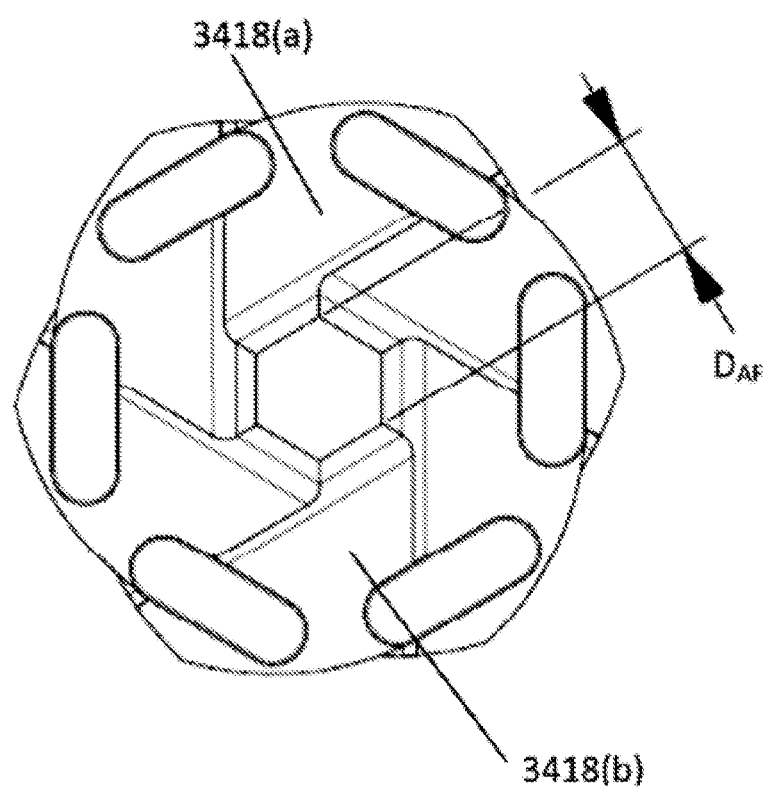

FIG. 7 shows a view of an example vent of the present technology;

FIG. 8 shows a view of the vent arrangement of FIG. 7 with an open central aperture;

FIGS. 9, 10 and 11 shows various exploded views of an example vent arrangement of the present technology with the central aperture of varying sizes;

FIGS. 12A and 12B show a portion of the vent 3400 from the exhaust side with closed and open central aperture respectively;

FIG. 13 also shows a portion of the vent from the exhaust side, showing leaves;

FIGS. 14A and 14B show a plurality of leaves arranged to form an adjustable central aperture with varying sizes;

FIG. 15 shows one of the plurality of leaves of FIG. 13;

FIG. 16 shows another view of the leaf of FIG. 15 including a cross sectional view taken along line A-A;

FIG. 17 shows a flow chart of an exemplary vent aperture sizing protocol for controlling the size of the aperture;

FIG. 18 shows an example flowchart for a vent sizing function;

FIG. 19 shows another example flowchart for a vent sizing function;

FIG. 20 shows another example flowchart for a vent sizing function;

FIG. 21 shows a flowchart for vent sizing using such a look-up table;

FIG. 22 shows an example patient interface with a set of locations of microphones or proximity sensors placed near a vent of the present technology or an accelerometer;

FIGS. 23A and 23B each illustrate vent aperture control to drive the vent through a calibration cycle; and FIG. 24 show leaves of a vent arrangement and a distance across opposing surfaces of two of the leaves.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

Therapy

In one form, the present technology comprises a method for treating a respiratory disorder comprising the step of applying positive pressure to the entrance of the airways of a patient 1000.

Nasal CPAP for OSA

In one form, the present technology comprises a method of treating Obstructive Sleep Apnea in a patient by applying nasal continuous positive airway pressure to the patient.

Patient Interface 3000

A non-invasive patient interface 3000 in accordance with one aspect of the present technology comprises the following functional aspects: a seal-forming structure 3100, a plenum chamber 3200, a positioning and stabilising structure 3300, a vent 3400 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

Seal-forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

Plenum Chamber 3200

Preferably the plenum chamber 3200 has a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

Positioning and Stabilising Structure 3300

Preferably the seal-forming portion 3100 of the patient interface 3000 of the present technology is held in sealing position in use by the positioning and stabilising structure 3300.

Vent 3400

In one form, the patient interface 3000 includes a vent 3400 constructed and arranged to allow for the washout of exhaled carbon dioxide.

One form of vent 3400 known in the prior art comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3500, e.g. a swivel 3510.

A vent device comprising one or a plurality of vents 3400 as described below may be located in the patient interface 3000, in the patient conduit 4170 or as a separate component configured to be coupled to a patient interface 3000 or a patient conduit 4170.

Vent Geometry

A vent arrangement according to an aspect of the current technology is shown in FIG. 7, showing a vent 3400 which comprises a plurality of blades, or leaves 3404 and an outer housing 3408.

A key aspect of the current technology is that the size of the central aperture 3422 of the vent 3400 may be adjusted between a predetermined maximum size to a predetermined minimum size. This vent 3400 may therefore allow for a flow of breathable gas to traverse into and out of the vent 3400 via its central aperture 3422 as shown in FIG. 8. Aspects of the air flow therethrough may be controlled by changing the size of the central aperture 3422.

Aspects of the air flow through the vent 3400 may be modified by changing properties of the vent 3400, such as the size of the central aperture 3422. Examples of aspects of the air flow through the vent 3400 that may modified by changing properties of the vent 3400, such as the size of the central aperture 3422 include the air impedance of the vent 3400 and/or characteristics of noise generated by the vent 3400.

One method of describing the size of the central aperture 3422 may be to describe it as a function of the distance 'across flats', which describes the distance across opposing surfaces of each leaf 3404. An example of this measurement is shown in FIG. 24, wherein the distance designated $D_{AF}$ between the outer leaf surface 3418(*a*) and the opposing outer leaf surface 3418(*b*) would be a distance 'across flats'.

FIG. 9 shows an exploded view of the vent 3400 comprising a plurality of leaves 3404, a common guiding member, or guide ring 3406, and an outer housing 3408. As illustrated the vent 3400 comprises 6 leaves 3404 but it is to be understood that the vent may comprise a different number of leaves 3404 as discussed in more detail below. The vent 3400 also may be connected to an actuating drive mechanism, which may comprise, for example, a magnet ring 3452 and a coil 3454. The actuating drive mechanism may take the form of any number of rotary or linear drive mechanisms, such as a linear actuator, a rotary actuator, a motor drive mechanism or any number of such means known in the art. The actuating drive mechanism may include the drive mechanism described in U.S. provisional patent application No. 61/699,520 filed on 11 Sep. 2012, the contents of which is incorporated herein in its entirety.

FIGS. 10-11 show further exploded views of the vent 3400 arrangement similar to those shown in FIG. 9, showing varying sizes of the central aperture 3422. FIGS. 9-11 also show that each leaf 3404 is coupled with the guide ring 3406. The guide ring 3406 includes a plurality of guide ring keys 3410 formed on the outer surface of the guide ring 3406 and are configured to each engage with a leaf guide slot formed on the surface of each of the plurality of leaves 3404. The opposing side of each of the plurality of leaves is configured to couple to the outer housing 3408. Each of the plurality of leaves 3404 includes a leaf protrusion 3414 located on the surface of each leaf 3404. Each leaf protrusion 3414 may be inserted into an outer housing guide slot 3416 formed in the outer housing 3408 as shown in FIG. 13.

FIGS. 12A-12B show a portion of the vent 3400 from the exhaust side, showing the plurality of leaves 3404 and the outer housing 3408 assembled together. These figures show the leaf guide slots 3412 that are formed on the exhaust side of each leaf 3404. Each guide slot 3412 is configured to receive a guide ring key 3410 as described above.

FIG. 13 also shows a portion of the vent 3400 from the exhaust side, showing the leaves 3404 and the outer housing 3408 prior to assembly. FIG. 13 shows an exploded view of the vent 3400 to display the outer housing guide slot 3416. It can be seen here that for an individual blade such as blade 3404(3) with guide slots 3412(3), its movement is defined as a linear path following the outer housing guide slot 3416 that the leaf protrusion 3414 (as seen in FIGS. 14A and 14B) inserts into, shown by the double-ended arrow in FIG. 13. The outer housing guide slot 3416 is shown in FIG. 13 as a single continuous recess formed integrally with the outer housing 3408, however it is to be understood that it may be formed as a plurality of discrete recesses, each configured to receive a leaf protrusion 3414.

FIGS. 14A and 14B show the plurality of leaves 3404 arranged to form an adjustable central aperture 4322 according to an example of the current technology, indicating two different possible sizes of the central aperture 3422. However, it is to be understood that the central aperture 3422 is configured to form a plurality of different sizes. FIG. 15 shows an example of one of the plurality of leaves according to an example of the present technology. In this example, the leaf protrusion 3414 is integrally formed as a part of the leaf 3404, however it should be understood that it may alternatively be formed as a separate component that may be coupled between each of the plurality of leaves 3404 and the outer housing 3408.

As the plurality of leaves 3404 are re-arranged from a closed configuration as shown in FIG. 14A to a more open configuration as shown in FIG. 14B, an outer leaf surface 3418 of one of the plurality of leaves 3404(1) slides relative to an inner leaf surface 3420 of an adjacent leaf 3404(2) of the plurality of leaves. The coordinated movement of each of the plurality of leaves 3404(1) against an adjacent leaf 3404(2) results in the opening and closing of the central aperture 3422.

Another aspect of the current technology is that it may allow for the central aperture 3422 to be adjusted from a predetermined maximum to a predetermined minimum. The predetermined minimum may be a zero cross sectional area, or it may be a small cross sectional area or any number of cross sectional areas, as will be described in more detail below. Another aspect of this technology is that the size of the central aperture 3422 is infinitely adjustable between the predetermined maximum and predetermined minimum levels, subject to the resolution to the control system and/or mechanism.

Furthermore, any number of leaves 3404 may be used to construct the vent 3400. Accordingly, shape of the leaves 3404, shape of the outer housing guide slot 3416 and the shape of the aperture 3422 is dependent on the number of leaves 3404 that are present in the vent 3400. For instance, the central aperture 3422 shown in FIG. 14B is in a hexagonal shape as the vent 3400 comprises six leaves 3404 in this configuration. Preferably between three and eight leaves 3404 may be used in the vent 3400, more preferably between four and six leaves 3404 may be used, although the number of leaves 3404 may vary as the design parameters and requirements vary, such as the size of the required aperture, material employed or the cross-section profile of the leaf 3404.

In this example of the current technology, each leaf guide slot 3412 is shaped as a rectangular slot with rounded internal corners. This facilitates slidable and rotatable movement of the corresponding guide ring key 3410 within each leaf guide slot 3412 when the plurality of leaves 3404 are moved to adjust the size of the central aperture 3422. In the example illustrated the guide ring keys 3410 form a protrusion on the guide ring 3406 that is inserted into the leaf guide slots 3412 on each of the plurality of leaves 3404.

However, in an alternative arrangement each of the plurality of leaves 3404 may comprise a protrusion or key (not shown) and the guide ring 3406 may comprise a slot or recess (not shown) that enables the slidable and rotatable movement of the protrusion or key located on each of the plurality of leaves 3404 as the plurality of leaves move. In a further alternative arrangement both of the guide ring 3406 and each of the plurality of leaves 3404 may include a slot or recess and a separate key component may be coupled therebetween. In a yet further alternative, both of the guide ring 3406 and each of the plurality of leaves 3404 may include protrusions or keys and a separate component comprising corresponding recesses or slots may be coupled therebetween.

On the opposite face of each of the plurality of leaves 3404, each leaf comprises a leaf protrusion 3414. The leaf protrusion 3414 may have a shape with rounded internal corners to facilitate slidable movement of each of the plurality of leaves 3404 relative to the outer housing 3408. As described above the outer housing 3408 includes an outer housing guide slot 3416 configured to receive the leaf protrusions 3414 from one of the plurality of leaves 3404 therein. The outer housing guide slot 3416 is larger than the size of the leaf protrusions 3414 to facilitate movement of the connecting plate protrusions along the outer housing guide slot 3416 when the plurality of leaves 3404 are moved to adjust the size of the central aperture 3422.

In an alternative arrangement, the outer housing 3408 may include a protrusion and each of the plurality of leaves may include a slot or recess that enables the slidable movement of the protrusions located on the outer housing 3408 within the slots or recesses on the plurality of leaves 3404 as the plurality of leaves 3404 move. In a further alternative arrangement both of the outer housing 3408 and each of the plurality of leaves 3404 may include a slot or recess and a separate connecting plate component may be coupled therebetween. In yet another alternative arrangement both of the outer housing 3408 and each of the plurality of leaves 3404 may include protrusions and a separate connecting component comprising recesses or slots may be coupled therebetween.

Control System

One exemplary means of controlling the size of the central aperture 3422 may be to rotationally fix the outer housing 3408 and to affix the guide ring 3406 to an actuator The actuator may comprise limit switches, and may be controlled by a vent aperture control system. In such a system, the limit switches may be used to determine when the size of the central aperture 3422 of the vent 3400 has reached the predetermined maximum or the predetermined minimum throughout its range of possible sizes.

One aspect of operation of the vent aperture control system may be to drive the vent 3400 through a calibration cycle. In one component of the calibration cycle, shown in FIG. 23A the actuator would open the vent 3400 until the size of the central aperture 3422 reaches at its maximum, upon which point the limit switch may detect an indicating signal such as the voltage supplied exceeding a threshold voltage, or the current supplied exceeding a threshold current, or the power supplied exceeding a threshold power, or a proximity sensor indicating that the vent is at its 'completely open' position. In another component of the calibration cycle, shown in FIG. 23B, actuator may progressively close the vent 3400 until the aperture 3422 reaches its minimum, upon which point the limit switch may detect an indicating signal such as those described above. Such a calibration cycle may thus provide the control system with accurate limits of travel for the aperture 3422.

Another aspect of the current technology is that the minimum size of the vent aperture 3422 may be as small as zero cross sectional area. Any number of sizes may be chosen for the minimum vent aperture 3422 size between, for example, 0.01 mm to 10 mm distance across flats, such as 0.1 mm, 0.5 mm or 1 mm, 2 mm or 3 mm distance across flats.

Cross-section Profile

An aspect of the above arrangement of the vent 3400 is that as the size of the aperture 3422 changes, the cross-section profile of each outer leaf surface 3420 that is exposed to the flow of breathable gas traversing through the vent remains constant, irrespective of the length of the inner leaf surface 3420 that is exposed to the flow of breathable gas.

As described above, some of the problems related to vent technologies in the prior art have been that it has been noisy for the patient 1000, and/or that they may be disruptive of the sleep of a bed-partner 1100 through noise or focussed airflow.

Another aspect of the present technology is the design of the cross-section profile 3424 of the inner leaf surface 3420 of each of the plurality of leaves 3404. The cross-section profile of each outer leaf surface 3420 that is exposed to the flow of breathable gas remains constant as the size of the central aperture 3422 changes. Therefore, the cross-section profile 3424 may be shaped at the leading edge 3426 and the trailing edge 3428 to reduce noise generated by the flow of breathable gas as it passes through the aperture 3422.

One example of a suitable cross-section profile may be a 'reverse-trumpet' profile, similar to one disclosed in the US patent application US 2010/0051034, the entire contents of which is incorporated herein by reference.

Such a profile may include a contracting, curved leading edge 3426 that blends into the entry side surface 3430 of each of the plurality of leaves 3404. The profile may further include a sharply terminating trailing edge 3428 at the exhaust side surface 3432 as shown in FIG. 16. The leading edge 3426 may approximate a contracting curved surface and connect to the trailing edge 3438, which may be curved and tangential to a centre axis of the aperture 3422 or converge at a small angle, such as between approximately 0 and approximately 15 degrees. The trailing edge may terminate with an angle of between approximately 60 degrees and approximately 100 degrees, such as 70 degrees, 80 degrees, or 90 degrees between the exit-side surface 3432 of the leaf 3404 and the trailing edge 3428.

The radius of the leading edge R2 may be between approximately 0.5 mm and approximately 1.5 mm, such as 0.75 mm, 1 mm or 1.25 mm, and the radius of the trailing edge R1 may be between approximately 1 mm and approximately 3 mm, such as 1.5 mm, 2 mm or 2.5 mm. The thickness T1 of each leaf 3404 may be between approximately 1 mm and approximately 4 mm, such as 2 mm, 2.5 mm or 3 mm. The convergence in section depth C1 of each of the plurality of leaves 3404 may be between approximately 0.5 mm and approximately 2.5 mm, such as 1 mm, 1.5 mm or 2 mm.

In one instance of the present technology, the vent 3400 may comprise of six leaves 3404, wherein the thickness T1 of each leaf 3404 may be about 1-4 mm, such as 2 mm, 2.5 mm or 3 mm, and the maximum distance across each opposing leaves (across flats) may be about 5-9 mm, such as 6 mm, 7 mm or 8 mm. In this arrangement, the vent 3400 with the aperture 3422 at the most open position would be approximately between 21 mm$^2$ and 70 mm$^2$ such as 30 mm$^2$, 40 mm$^2$, 50 mm$^2$ or 60 mm$^2$ depending on the distance across flats and at 7 mm distance across flats (AF) the area of the aperture 3422 may be approximately 42 mm$^2$.

Another aspect of the present technology is that characteristics of noise generated by the flow of breathable gas through the vent 3400 may change as the size of the central aperture 3422 changes. One example of such a noise characteristic is the level of noise generated, although other characteristics such as the frequency content of the noise may also change. An example showing changes to the measured sound power level as a function of the aperture 3422 size (distance across flats) and/or the pressure is shown. For example, at approximately 10 cm $H_2O$ of pressure, the measured sound power level of the vent 3400 was approximately 30 dBA when the vent 3400 was configured with a distance across flats of approximately 4 mm. When the vent 3400 was in another configuration with a distance across flats of approximately 7 mm, the measured sound power level was approximately 32 dBA.

The dimensions of the vent 3400 may vary under different design circumstances, such as the number of vents 3400 to be placed on a patient interface 3000, or varying therapy requirements. As a result, the dimensions as described above should be understood to be only exemplary and a person skilled in the art would be capable of changing any number of the above dimensions of the vent 3400 to suit their requirements.

Sensor-driven Active Vents

In another aspect of the current technology, multiple instances of the vents 3400 described above may be placed on a patient interface 3000 such as in the plenum chamber 3200 or in a decoupling structure 3500, or in the patient conduit 4170. The size of their apertures 3422 may then be controlled together or separately to control various properties of the flow of breathable gas communicating through the patient interface 3000, such as noise generated or directionality of the flow. This may be carried out by controlling the noise generated from the flow of breathable gas through each vent 3400 or controlling the amount of flow through the vent, for example during different phases of the respiratory cycle. For example, the vents may be configured to open only during the expiration phase of the respiratory cycle.

In one example of this technology, two vents 3400 may be placed on either side of the patient interface 3000 as shown in FIG. 22 so that they are approximately symmetrical about the sagittal plane once the patient 1000 puts on the patient interface 3000.

One method of achieving said noise reduction may be to control the size of the aperture 3422 of each vent 3400 according to a predetermined control parameter. One example of such a control parameter may be measured noise levels from microphones 3440 placed near each vent 3400. In another example of a suitable control parameter may be an output from an accelerometer 3442, which may be processed to indicate an orientation of the patient 1000. Other suitable control parameters may include, pressure, flow, temperature, respiratory phase, such as whether the patient is in inspiration or in expiration, or therapy-related parameters, such as the patient's SpO2 level or whether the patient suffers from CSR.

An exemplary set of locations of microphones 3440 or proximity sensors 3444 placed near each vent 3400 or an accelerometer 3442 is shown in FIG. 22, however it is to be understood that the numbers and locations of the vents 3400, the microphones 3440, or accelerometers 3442 may be varied. Any number of other sensors known in the art, such as pressure, temperature or flow sensors may be used to provide one or more control parameters.

FIG. 17. shows a flow chart of an exemplary vent aperture sizing protocol for controlling the size of the aperture 3422 of each vent 3400 as a function of one or more control parameters. One example of the protocol's function may be as follows. It may first determine value(s) of the control parameter comprising, for example, noise levels as measured by the microphones 3440 placed near each vent 3400 and/or a signal indicating the orientation of the patient 1000, or other inputs as described above. The vent aperture sizing protocol would determine desired opening sizes for apertures 3422 based on the value(s) of the control parameter(s). This may be carried out using a look-up table or a predetermined vent sizing function configured to determine desired changes to vent sizing based on the inputs of the value(s) of the control parameter(s). The vent aperture sizing protocol would then communicate the desired aperture opening sizes to the control system 3438 to adjust the sizes of each vent apertures 3422 accordingly.

One example of a vent sizing function is shown as a flowchart in FIG. 18 In this example, the vent sizing function may open both vents 3400 to ensure equal operating conditions, and then measure noise levels (N1 and N2) at two microphones 3440 that are placed near each vent 3400. The vent sizing function may compare the noise levels N1 and N2, and act to close or partially close the vent 3400 that is creating more noise.

Another example of a vent sizing function is shown as a flowchart in FIG. 19. In this example, the vent sizing function may receive two noise levels (N1 and N2) from two microphones 3440 that are placed near each vent 3400. It may also receive areas of apertures 3422 (S1 and S2) from each vent 3400. The vent sizing function would compare the noise levels N1 and N2, and act to reduce the size of the aperture 3422 of the corresponding vent 3400 where the noise level was found to be higher, and increase the size of the aperture 3422 of the corresponding vent 3400 where the noise level was found to be lower. The size of the aperture 3422 of each vent 3400 may be adjusted by a predetermined increment until the noise levels N1 and N2 are substantially equal to each other, or until the difference in noise levels is under a predetermined threshold.

In the examples of the vent sizing functions described above, the function may also compare the noise levels N1 and N2 against a threshold value $N_{threshold}$ as to only adjust the sizes of the vent apertures 3422 if one or both values are above and/or below $N_{threshold}$.

A yet another example of a vent sizing function is shown as a flowchart in FIG. 20. In this example, the vent sizing function may receive a signal indicating at least one of the orientation of the patient 1000 or the orientation of the patient interface 3000 from an accelerometer 3442. The vent sizing function may then send a signal to the vents 3400 to reduce the size of the aperture 3422 of the corresponding vent 3400 which is closer to the ground, and increase the size of the aperture 3422 of the corresponding vent 3400 which is further from the ground. This may reduce the noise generated by the patient interface 3000 as impingement of the flow of breathable gas upon an obstruction such a pillow, or bedding is known to generate additional noise in comparison to the unobstructed flow of breathable gas exiting the vent 3400 exits into the atmosphere.

Furthermore, using the above technology it may also be possible to reduce the amount of exiting flow of breathable gas from a vent 3400 that is directed at a bed partner 1100, which may reduce annoyances and/or additional noise experienced by the bed partner.

In another example of the present technology, the vent sizing function may receive a signal from a proximity sensor 3444 indicating the proximity of the patient 1000 to its bed partner 1100 or another obstruction to each vent 3400 in the direction of its aperture 3422. The vent sizing function may then act to reduce the size of the aperture 3422 of the corresponding vent 3400 which is closer to the bed partner 1100 or obstruction, and increase the size of the aperture 3422 of the corresponding vent 3400 which is further from the bed partner 1100 or obstruction. It is to be understood that the vent sizing function may also receive and react to a signal other types of sensors, such as from a modulated pulse Doppler based sensor such as one disclosed in U.S. Pat. No. 6,426,716 or a sensor described in US patent application number 2009/0203972, the entire contents of which are included herein by reference.

In a yet another example of the current technology, the vent sizing function may receive and react to a signal indicating whether the patient 1000 is in inspiration or in expiration. According to this signal the vent sizing function may, for example, close the vent 3400 during the inspiration phase of the patient's breath, and open the vent 3400 during the expiration phase of the patient's breath.

Although a number of above paragraphs discuss means of determining sizes of apertures 3422 of vents 3400 using a vent sizing function, it should be understood that this may be achieved by use of a multi-dimensional look-up table by themselves or in conjunction with a vent sizing function. It should also be clear to those skilled in the art that while the above describes examples of the current technology that utilise two vents 3400, any number of vents 3400 may be used.

In an exemplary instance of the current technology that utilises a look-up table, it may receive a differential noise value Nd, which is calculated as the difference between the two noise levels measured by the microphones 3440 placed near each vent 3400. Ranges may be given for Nd in such a look-up table so that the size of the aperture 3422 may be adjusted for each vent 3400 according to Nd, and the amount by which to adjust the size of the aperture 3422 (ΔArea) may be also inferred from the look-up table. FIG. 21 shows an exemplary instance of a flow chart using such a look-up table.

It is to be understood that the control protocols and means described above are not to be limited only to the instance of the current vent technology. An equivalent performance to adjusting sizes of vent apertures 3422 of multiple vents 3400 according to sensor inputs may be also performed by a single vent assembly that allows the flow of breathable air to be re-directed. For instance, a single vent assembly that allows movement of its aperture along the sagittal plane may allow the vent to direct its outflow to the left or the right side of the patient 1000 according to a sensor input as described above.

Decoupling Structure(s) 3500

In one form the patient interface 3000 includes at least one decoupling structure 3500, for example a swivel 3510 or a ball and socket 3520.

Connection Port 3600

Connection port 3600 allows for connection to the air circuit 4170.

Forehead Support 3700

In one form, the patient interface 3000 includes a forehead support 3700.

Anti-Asphyxia 3800

In one form, the patient interface 3000 includes an anti-asphyxia valve 3800.

Ports 3900

In one form of the present technology, a patient interface 3000 includes one or more ports 3900 that allow access to the volume within the plenum chamber 3200. In one form this allows a clinician to supply supplemental oxygen. In one form this allows for the direct measurement of a property of gases within the plenum chamber 3200, such as the pressure.

Glossary

In certain forms of the present technology, one or more of the following definitions may apply. In other forms of the present technology, alternative definitions may apply.

General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A vent device suitable for use with a respiratory device for delivering a supply of air or breathable gas to the entrance of a patient's airways for the amelioration or treatment of a respiratory disorder comprising:
   a first vent comprising a first size adjustable central aperture on a plenum chamber of a mask;
   a second vent comprising a second size adjustable central aperture on the plenum chamber of the mask with said first vent;
   a first actuator assembly on the mask to automatically vary a first property of the first vent in response to a first control system signal for adjusting the central aperture of the first vent; and
   a second actuator assembly on the mask to automatically vary a second property of the second vent in response to a second control system signal for adjusting the central aperture of the second vent,
   wherein a size of the central aperture of the first vent and a size of the central aperture of the second vent are configured to be controlled by a control system configured to control an operation of the first actuator assembly and the second actuator assembly, and wherein the operation is configured to change the size of the central aperture of the first vent distinctly from the size of the central aperture of the second vent by coordinating (a) an increase in size of the central aperture of one of the first vent and the second vent, with (b) a decrease in size of the central aperture of the other one of the first vent and the second vent.

2. The vent device of claim 1, wherein the first property of the first vent and/or the second property of the second vent are impedance values to a flow of air or breathable gas passing therethrough.

3. The vent device of claim 1, wherein the first property of the first vent and/or the second property of the second vent are cross-sectional areas for a flow of air or breathable gas to pass therethrough.

4. The vent device of claim 1, further comprising:
a sensor adapted to generate a first signal, and
wherein the first signal is processed to determine the first property of the first vent and/or the second property of the second vent to generate the first control system signal.

5. The vent device of claim 1 configured to couple with a patient conduit or a patient interface.

6. A patient interface comprising the vent device as claimed in claim 1.

7. A patient conduit comprising the vent device as claimed in claim 1.

8. The vent device of claim 1, wherein the operation is configured to result in the increase in size of the central aperture of the one vent simultaneously with a decrease in size of the central aperture of the other vent.

9. A vent device suitable for use with a respiratory device for delivering a supply of air or breathable gas to the entrance of a patient's airways for the amelioration or treatment of a respiratory disorder comprising:
a first vent configured with a first variable cross-section area on a plenum chamber of a mask for communicating a flow of breathable gas, the first vent including a first actuator assembly on the mask to automatically vary the first variable cross-section area in response to a first control system signal for adjusting the first variable cross-section area;
a second vent configured with a second variable cross-section area on a plenum chamber of the mask with the first vent, the second vent including a second actuator assembly on the mask to automatically vary the second variable cross-section area in response to a second control system signal for adjusting the second variable cross-section area;
a control system configured to set the first vent and the second vent; and
a first sensor configured to output a first signal;
wherein the vent device is configured so that the first cross-section area and/or the second cross-section area are determined as a function of the first signal,
wherein the control system is configured to control an operation of the first actuator assembly and the second actuator assembly, and wherein the operation is configured to change a size of the central aperture of the first vent distinctly from a size of the central aperture of the second vent by coordinating (a) an increase in size of the cross-section area of one of the first vent and the second vent, with (b) a decrease in size of the cross section area of the other one of the first vent and the second vent.

10. The vent device of claim 9, further comprising a second sensor configured to output a second signal, wherein the first signal indicates a noise level of the first vent and the second signal indicates a noise level of the second vent, and the first cross-section area is determined as a function of the first signal, and the second cross-section area is determined as a function of the second signal.

11. A patient interface comprising the vent device as claimed in claim 10.

12. The vent device of claim 10, wherein the first signal is generated by a first microphone and the second signal is generated by a second microphone.

13. The vent device of claim 9, wherein the first signal indicates an orientation of the vent device.

14. The vent device of claim 13, wherein the first signal is generated by an accelerometer.

15. The vent device of claim 9, wherein the first signal indicates a pressure of the flow of the supply of breathable gas.

16. The vent device of claim 9, wherein the first signal indicates a flow rate of the supply of breathable gas.

17. The vent device of claim 9, wherein the first vent and the second vent each comprise:
a plurality of leaves forming a controlled variable size area for communication of a flow of breathable gas therethrough from a plenum chamber of the mask to atmosphere, the plurality of leaves forming a surface around the area; and
the cross-section profile of each outer leaf surface that is exposed to the flow of breathable gas traversing therethrough remains constant as the size of the area is varied.

18. The vent device of claim 17 configured to couple with a patient conduit or a patient interface.

19. A patient interface comprising the vent device as claimed in claim 17.

20. A patient conduit comprising the vent device as claimed in claim 17.

21. The vent device of claim 9 configured to couple with a patient conduit or a patient interface.

22. A patient interface comprising the vent device as claimed in claim 9.

23. A patient conduit comprising the vent device as claimed in claim 9.

24. The vent device of claim 9, wherein the first cross-section area is set to be a different area from the second cross-section area.

25. A patient interface of claim 24 wherein the first vent and the second vent are located on different sides of the patient interface so that they are approximately symmetrical about a sagittal plane of the patient interface.

26. The vent device of claim 9, wherein the operation is configured to result in the increase in size of the central aperture of the one vent simultaneously with a decrease in size of the central aperture of the other vent.

27. The vent device of claim 9, wherein the operation is configured to result in the increase in size of the central aperture of the one vent and the decrease in size of the central aperture of the other vent based on a comparison of the first signal with the second signal.

* * * * *